(12) United States Patent
Bae et al.

(10) Patent No.: US 11,571,460 B2
(45) Date of Patent: Feb. 7, 2023

(54) COMPOSITION INCLUDING MELITTIN FOR REMOVING M2-TYPE TUMOR-ASSOCIATED MACROPHAGE

(71) Applicant: LENUS LAB, Seoul (KR)

(72) Inventors: Hyunsu Bae, Seoul (KR); Chan-Ju Lee, Goyang-si (KR)

(73) Assignee: LENUS LAB, Hanam-si (KR)

( * ) Notice: Subject to any disclaimer, the term of this patent is extended or adjusted under 35 U.S.C. 154(b) by 0 days.

(21) Appl. No.: 16/641,121

(22) PCT Filed: Apr. 30, 2018

(86) PCT No.: PCT/KR2018/005003
§ 371 (c)(1),
(2) Date: Feb. 21, 2020

(87) PCT Pub. No.: WO2019/039700
PCT Pub. Date: Feb. 28, 2019

(65) Prior Publication Data
US 2020/0206311 A1    Jul. 2, 2020

(30) Foreign Application Priority Data
Aug. 23, 2017    (KR) ........................ 10-2017-0106939

(51) Int. Cl.
*A61K 38/00*    (2006.01)
*A61K 38/17*    (2006.01)
*A61P 35/00*    (2006.01)

(52) U.S. Cl.
CPC .......... *A61K 38/1767* (2013.01); *A61P 35/00* (2018.01)

(58) Field of Classification Search
CPC .... A61K 35/63; A61K 38/16; A61K 38/1767; A61K 35/00
See application file for complete search history.

(56) References Cited

PUBLICATIONS

Huh et al. Melittin Suppresses VEGF-A-Induced Tumor Growth by Blocking VEGFR-2 and the COX-2-Mediated MAPK Signaling Pathway. 2012. J. Nat. Prod. 2012, 75, 11, 1922-1929. (Year: 2012).*

Kloepper et al. Ang-2/VEGF bispecific antibody reprograms macrophages and resident microglia to anti-tumor phenotype and prolongs glioblastoma survival. Proc Natl Acad Sci U S A. Apr. 19, 2016; 113(16): 4476-4481. (Year: 2016).*

Amboss—local inflammatory responses. Accesses Oct. 28, 2020 at https://www.amboss.com/us/knowledge/Local_inflammatory_responses#:~:text=Inflammation%20is%20the%20response%20of,be%20either%20acute%20or%20chronic.. (Year: 2020).*

Lee et al. Anti-Inflammatory Applications of Melittin, a Major Component of Bee Venom: Detailed Mechanism of Action and Adverse Effects. Molecules 2016, 21, 616. (Year: 2016).*

Shaw et al. Synergistic Effects of Melittin and Plasma Treatment: A Promising Approach for Cancer Therapy. 2019. Cancers (Basel). Aug. 2019; 11(8): 1109. (Year: 2019).*

Soliman et al. The membrane effects of melittin on gastric and colorectal cancer. 2019. PLoS One. 2019; 14(10): e0224028. (Year: 2019).*

Ceremuga et al. Melittin—A Natural Peptide from Bee Venom Which Induces Apoptosis in Human Leukaemia Cells. Biomolecules 2020, 10, 247;. (Year: 2020).*

Noy et al. Tumor-associated macrophages: from mechanisms to therapy. Immunity. Jul. 17, 2014; 41(1): 49-61. (Year: 2014).*

Gao et al. The relationship between the inhibitory effect of melittin (Mel) on osteosarcoma in nude mice and its influence on tumor angiogenesis, cell proliferation and apoptosis. Journal of Fudan University (Medical Edition) 2012, vol. 39, Issue 3 pp. 283-288 (Year: 2012).*

Zhang et al. Melittin exerts an antitumor effect on non-small cell lung cancer cells. Molecular Medicine Reports 16: 3581-3586, 2017 (Year: 2017).*

Chanju Lee, "Melittin suppresses tumor progression and angiogenesis by regulating tumor-associated macrophages (TAMs) in Lewis lung carcinoma mice model", Master's Thesis, Graduate School of Kyung Hee University, Aug. 2016, pp. 1-61.

Chen Wang, et al., "Melittin, a Major Component of Bee Venom, Sensitizes Human Hepatocellular Carcinoma Cells to Tumor Necrosis Factor-related Apoptosis-inducing Ligand (TRAIL)-induced Apoptosis by Activating CaMKII-TAK1-JNK/p38 and Inhibiting IκBα Kinase-NFκB*", The Journal of Biological Chemistry, 2009, pp. 3804-3813, vol. 284, No. 6.

Jeremy S. Tilstra, et al., "Pharmacologic IKK/NF-κB inhibition causes antigen presenting cells to undergo TNFα dependent ROS-mediated programmed cell death", Scientific Reports, Jan. 10, 2014, pp. 1-11, vol. 4, thesis No. 3631.

Hye Ji Park, et al., "Melittin inhibits inflammatory target gene expression and mediator generation via interaction with IkB kinase", Biochemical Pharmacology, 2007, pp. 237-247, vol. 73.

(Continued)

*Primary Examiner* — Aradhana Sasan
*Assistant Examiner* — Mercy H Sabila
(74) *Attorney, Agent, or Firm* — Sughrue Mion, PLLC

(57) ABSTRACT

The present invention relates to a composition including melittin as an active ingredient for removing an M2-type tumor-associated macrophage (TAM), and more specifically, the present invention relates to a composition exhibiting an effect of selectively suppressing only M2-type tumor-associated macrophages among tumor-associated macrophages. The composition according to the present invention only suppresses M2-type tumor-associated macrophages without affecting M1-type tumor-associated macrophages or cancer cells, thus exhibiting anti-cancer and metastasis suppressing effects by blocking angiogenesis through control of the microenvironment of cancer cells, while reducing the side-effects of existing anti-cancer effects.

4 Claims, 30 Drawing Sheets
Specification includes a Sequence Listing.

(56) References Cited

PUBLICATIONS

Camila G. Dantas, et al., "Pharmacological evaluation of bee venom and melittin", Revista Brasileira de Farmacognosia, 2014, pp. 67-72, vol. 24.

Chanju Lee, et al., "Melittin suppresses tumor progression by regulating tumor-associated macrophages in a Lewis lung carcinoma mouse model" Oncotarget, 2017, pp. 54951-54965, vol. 8, No. 33.

Chanju Lee, et al., "Melittin suppresses tumor progression by regulating tumor-associated macrophages in a Lewis lung carcinoma mouse model" The Journal of Immunology, May 1, 2017, pp. 1-3, vol. 198, No. (1 Supplement).

Chanju Lee, et al., "Melittin Suppresses Tumor Progression by Regulating Tumor-associated Macrophages in a Lewis Lung Carcinoma Mouse Model", In: Immunology 2017, May 12-16, 2017, p. 690 205.2.

Chanju Lee, et al., "Melittin Suppresses Tumor Progression by Regulating Tumor-associated Macrophages in a Lewis Lung Carcinoma Mouse Model", The Journal of Immunology, Jun. 12, 2017, pp. 1-3, vol. 198, No. 1.

International Search Report for PCT/KR2018/005003 dated Aug. 24, 2018 [PCT/ISA/210].

Written Opinion for PCT/KR2018/005003 dated Aug. 24, 2018 [PCT/ISA/237].

\* cited by examiner

COMPOSITION INCLUDING MELITTIN FOR REMOVING M2-TYPE TUMOR-ASSOCIATED MACROPHAGE

CROSS REFERENCE TO RELATED APPLICATIONS

This application is a National Stage of International Application No. PCT/KR2018/005003 filed Apr. 30, 2018, claiming priority based on Korean Patent Application No. 10-2017-0106939 filed Aug. 23, 2017, the entire of which are incorporated herein by reference.

TECHNICAL FIELD

The present invention relates to a composition including melittin as an active ingredient for removing an M2-type tumor-associated macrophage (TAM) and more particularly, the composition of the present invention is an invention relating to a composition only suppresses M2-type tumor-associated macrophages without affecting M1-type tumor-associated macrophages or cancer cells and blocks angiogenesis through control of the microenvironment of cancer cells, thereby exhibiting anti-cancer and metastasis suppressing effects by reducing the side-effects of existing anti-cancer effects.

BACKGROUND ART

Conventional anti-cancer therapies have been studied to enhance the activity of immune cells in the body that attack cancer cells or to attack directly cancer cells. However, these anti-cancer drugs also attack other normal cells other than cancer cells, resulting in many side-effects such as hair loss, nausea, and vomiting, and cause additional reactions due to an excessive increase of immune cells. Therefore, it has been accelerated to develop a therapeutic agent having an anti-cancer effect by controlling only the surrounding microenvironment of the tumor cells without directly affecting tumor cells and immune cells to block nutrient supply to tumor cells and angiogenesis around the tumor cells.

The tumor microenvironment is greatly considered as a therapeutic target by contributing to the proliferation and survival of malignant cells, angiogenesis, metastasis, abnormally adaptive immunity, and reduced responses to hormones and chemotherapeutic agents. In many studies, it was demonstrated that the tumor-associated macrophage (TAM) is a major factor in the tumor microenvironment and an important regulator of angiogenesis, which is essential for tumor progression by supplying oxygen and nutrients to hypoxic tumor sites. Therefore, when a large number of tumor-associated macrophages exist around tumors in cancer patients, it has been reported that the prognosis and survival rate of patients are poor. The role of tumor-associated macrophages in the tumor microenvironment is still very controversial.

The tumor-associated macrophages are classified into two phenotypes of tumor suppressor M1 or tumor support M2 macrophages. The M1-type tumor-associated macrophage has a strong ability to present an antigen and generally presents CD86 and TNF-α. In contrast, the M2-type tumor-associated macrophage has a low antigen-presentation ability and high phagocytosis.

The M2-type macrophages are known to promote immunosuppression, tumorigenesis, and vasculogenesis by releasing various extracellular matrix components, angiogenesis and chemotaxis factors. The M2-type tumor-associated macrophages are distinguished from the M1-type tumor-associated macrophages by expressing some markers such as CD163, CD204, CD206, and IL-10. In most tumors, such as breast, ovarian, prostate, lung cancer and skin melanoma, the tumor microenvironment includes IL-10 capable of inducing the introduction of CSF-1, VEGF, CCL2, IL-4, IL-13, TGF-β and monocytes and inducing differentiation with a similar phenotype to M2. Previous studies have shown that depletion of macrophages by encapsulated clodronates may reduce angiogenesis in tumor tissues. In addition, since the infiltration of the macrophages is prevented through CSF-1R and CCR2 antibodies, it is possible to reduce tumor-initiating properties and increase the activity of cytotoxic T lymphocytes. Therefore, when a large amount of M2-type tumor-associated macrophages are present in the tumor microenvironment, the growth, differentiation, and metastasis of the tumor are activated, and thus the M2-type tumor-associated macrophages are targeted to lead to potential therapies to prevent tumor growth and metastasis.

Melittin is a major ingredient of the bee venom of *Apis mellifera* L. and an amphipathic peptide with 26 amino acid residues. The melittin has membrane-perturbing effects such as pore formation, fusion, and vesicle formation. The melittin has been used in tumor-bearing rat studies because of the ability of suppressing cytotoxicity and cell growth for tumor cells or inducing apoptosis and necrosis (Cancer Immunol Immunother. 2004; 53:411-421). However, the melittin is a very nonspecific cytolytic peptide and may cause an off-target effect that attacks all lipid membranes and destroys the membranes of normal cells. Meanwhile, there is a research that low-dose melittin may prevent pore formation. It has been reported that the melittin has the ability to neutralize the inflammatory activity of macrophages by regulating intracellular factors such as p50 and IκB kinase-α. In addition, it has also been found that the melittin interacts with LPS to inhibit the activation of LPS-induced macrophages and the production of inflammatory cytokine (Biochim Biophys Acta. 2007; 1768:3282-3291.).

In addition, as conventional techniques using melittin, a composition for treating arteriosclerosis containing melittin (Application No.: 10-2011-0117789), a composition for inhibiting the activity of fibroblast-like synoviocytes containing melittin (Application No.: 10-2011-0117788), etc. have been known.

In addition, as a technique related to immune cells of the bee venom containing melittin, a pharmaceutical composition (Registration No. 10-149167) for treating or preventing diseases associated with degradation of dysregulatory T cell activity containing bee venom-PLA2 is known, but just described for the association between a PLA2 ingredient other than melittin among main ingredients of the bee venom and immune cells. In addition, a composition (Registration No. 10-1146718) for preventing or treating angiogenesis-related diseases, lung cancer or pain containing a bee venom extract as an active ingredient is known and it is known that the bee venom may be used for the treatment of diseases such as cancer, but the detailed mechanism is unknown.

Thus, the role of melittin in the regulation of macrophage activity in the tumor microenvironment is not yet known. Therefore, the present inventors found that melittin suppressed only CD206$^+$ tumor-associated macrophages as M2-type tumor-associated macrophages without affecting CD86$^+$ tumor-associated macrophages as M1-type tumor-associated macrophages and cancer cells in a Lewis lung carcinoma (LLC) mouse model and completed the present invention which significantly reduced side-effects due to existing anti-cancer agents.

DISCLOSURE

Technical Problem

An object of the present invention is to provide a composition including melittin as an active ingredient for removing a tumor associated macrophage (TAM).

Another object of the present invention is to provide a pharmaceutical composition for treating tumor-associated macrophage-mediated diseases, including melittin or a pharmaceutically acceptable salt thereof as an active ingredient.

Yet another object of the present invention is to provide a method for removing tumor-associated macrophages including administering a composition including melittin or a pharmaceutically acceptable salt thereof as an active ingredient to a subject in need thereof.

Still another object of the present invention is to provide a method for preventing or treating tumor-associated macrophage-mediated diseases including administering a composition including melittin or a pharmaceutically acceptable salt thereof as an active ingredient for removing tumor-associated macrophages to a subject in need thereof.

Still yet another object of the present invention is to provide use of melittin or a pharmaceutically acceptable salt thereof for preparation of a pharmaceutical composition for preventing or treating tumor-associated macrophage-mediated diseases.

Technical Solution

In order to solve the problems, an aspect of the present invention provides a composition including melittin as an active ingredient for removing selectively tumor-associated macrophages, particularly an M2-type tumor-associated macrophage. Another aspect of the present invention provides a pharmaceutical composition for treating tumor-associated macrophage-mediated diseases, including melittin or a pharmaceutically acceptable salt thereof as an active ingredient. Yet another aspect of the present invention provides a method for removing tumor-associated macrophages including administering a composition including melittin or a pharmaceutically acceptable salt thereof to a subject in need thereof. Still another aspect of the present invention provides a method for preventing or treating tumor-associated macrophage-mediated diseases including administering a composition including melittin or a pharmaceutically acceptable salt thereof to a subject in need thereof. Still yet another aspect of the present invention provides use of melittin or a pharmaceutically acceptable salt thereof for preparation of a pharmaceutical composition for preventing or treating tumor-associated macrophage-mediated diseases.

Hereinafter, the present invention will be described in more detail.

Meanwhile, each description and embodiment disclosed in the present invention can also be applied to each of other descriptions and embodiments. That is, all combinations of the various components disclosed in the present disclosure belong to the scope of the present disclosure. In addition, the scope of the present disclosure may not be limited by the specific description described below.

Further, those skilled in the art may recognize or determine a plurality of equivalents to specific embodiments of the present disclosure described in the present disclosure by using only a general experiment. In addition, such equivalents are intended to be included in the present disclosure.

In a composition of the present invention to solve the problems, melittin may selectively suppress only M2-type tumor-associated macrophages without affecting M1-type tumor-associated macrophages and cancer cells. That is, the melittin suppresses only gene and protein expression of an M2-type phenotype marker without affecting an M1-type phenotype marker to increase a ratio (M1/M2) of M2-type tumor-associated macrophages to M1-type tumor-associated macrophages. Further, the present invention may provide a composition for suppressing tumor-associated macrophages which exhibits anti-cancer and metastasis suppressing effects by blocking angiogenesis through control of the microenvironment of cancer cells, while reducing side-effects of existing anti-cancer effects. The term "melittin" used herein is a peptide that constitutes a main ingredient of bee venom. The term "bee venom (BV)" used herein is a mixture of acidic and basic secretions produced in the abdomen of *Apis mellifera* and has a colorless bitter liquid form, and main ingredients thereof include melittin, apamin, and mast cell degranulating (MCD) peptide as peptides, phospholipase A2 (PLA2) as an enzyme, and the like, and further include various trace ingredients. Therefore, the melittin of the present invention may be isolated from the bee venom of Apis mellifera, but is not limited thereto.

The term "removal" used herein refers to the killing of the corresponding cells and includes the extent of removing only a part of the cells in addition to complete removal in the range thereof.

The term "tumor-associated macrophage (TAM)" used herein is a macrophage that plays an important role in the overall tumor microenvironment such as growth and metastasis of cancer and the tumor-associated macrophages existing around the tumor is closely associated with the growth and metastasis of tumor cells. The tumor-associated macrophages are classified into two phenotypes of tumor suppressive M1 or tumor support M2 macrophages. The M2-type tumor-associated macrophages produce cytokines such as IL-10, TGFβ, and CCL18 that promote the growth of cancer and serve to suppress the anti-tumor activity of T cells and NK cells by surface receptors. These tumor-associated macrophages may be differentiated from monocytes and macrophages developed in the bone marrow, the yolk sac or the extramedullary hematopoiesis, particularly in the spleen, and preferably, may be isolated from the bone marrow, but the present invention is not limited thereto.

In one embodiment of the present invention, it was found that the melittin does not affect the cell cycle of tumor cells (Example 4-2), and a tumor growth suppressing effect of the melittin is closely associated with tumor-associated macrophages (Example 6-2). In another embodiment of the present invention, it was confirmed that the melittin selectively binds to the M2-type tumor-associated macrophages to suppress the M2-type tumor-associated macrophages (Example 6-2) and a ratio of M1-type tumor-associated macrophages/M2-type tumor-associated macrophages is lowered (Example 7). Therefore, it could be confirmed that the melittin selectively binds to only the M2-type tumor-associated macrophages without inhibiting tumor cells and other immune cells to suppress the tumor growth and metastasis.

The term "vascular endothelial growth factor (VEGF)" used herein is a signal protein that stimulates vasculogenesis and angiogenesis and is a part of a system that compensates for the lack of oxygen caused in the blood vessels. The main function of this factor is to form blood vessels during fetal development and to form new blood vessels to replace damaged blood vessels, and it is reported that when this factor is excessively expressed, the factor causes breast cancer, external tumors, and ovarian cancer.

The term "Mrc1/CD205" used herein is a form in which a CD205 antibody binds to a mannose receptor C1 (Mrc1). Therefore, the term "Mrc1" used herein is a transmembrane-type endocytosis receptor, which is a kind of mannose receptor, and is present in a monomer to have a repeat structure of eight C-type lectin regions outside the cell. The mannose receptors are mainly present in mature macrophages, and Mrc1 mediates phagocytosis by recognizing sugars of a microorganism. These mannose receptors have a common extracellular domain structure, but types of the mannose receptors are distinguished in their unique ligand binding properties and cell type expression.

In one embodiment of the present invention, since the melittin reduces the expression of M2 genes such as the VEGF and Mrc1/CD206 in the bone marrow-derived macrophages and does not change the expression of M1 genes such as Vegf and flt1/VEGFR in Lewis lung carcinoma cells, it has been confirmed that the melittin may selectively reduce only the M2 genes and has a potential anti-angiogenesis effect. It was also confirmed that the treatment of melittin does not suppress the functional properties of macrophages such as ROS production and phagocytosis (Example 8-6).

The term "CD31" used herein is also known as platelet endothelial cell adhesion molecule-1 (PECAM-1) and is a Type I integral membrane glycoprotein of 140 kDa that is expressed at a high level in early and mature endothelial cells, platelets, and most leukocyte subpopulations. The expression in endothelial cells is concentrated in junctions between adjacent cells. The CD31 is also expressed in major populations of macrophage/dendritic cell precursors in the bone marrow. The CD31 is known to play various roles in vascular biology such as angiogenesis, platelet functions, and thrombosis.

In one embodiment of the present invention, it was confirmed that when the melittin is treated to the tumor tissue, the melittin reduces the levels of VEGF and CD31 (Example 9-2). This suggests that a decrease in population of tissue-resident M2-type tumor-associated macrophages suppresses angiogenesis. Therefore, it was confirmed that the melittin controls the tumor microenvironment to reduce the number of M2-type tumor-associated macrophages to exhibit an anti-cancer effect by suppressing angiogenesis around the tumor cells.

The composition including the bee venom extract of the present invention may further contain a pharmaceutically acceptable carrier.

The pharmaceutically acceptable carrier is generally used in preparation and includes lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methylcellulose, methylhydroxybenzoate, propylhydroxybenzoate, talc, magnesium stearate, and mineral oil, but is not limited thereto.

The composition of the present invention may further include a lubricant, a wetting agent, a sweetening agent, a flavoring agent, an emulsifying agent, a suspending agent, a preservative, and the like in addition to the above ingredients. Suitable pharmaceutically acceptable carriers and formulations are described in detail in Remington's Pharmaceutical Sciences (19$^{th}$ed., 1995). The composition of the present invention is formulated by using a pharmacologically acceptable carrier and/or excipient according to a method that may be easily performed by those skilled in the art to be prepared in a unit dose form or prepared by introduction into a multi-dose container. In this case, the formulation may also be a form of solutions, suspensions, or emulsions in oils or aqueous media or a form of excipients, powders, granules, tablets or capsules, and may additionally include a dispersant or a stabilizer.

The term "administration" used herein means providing a predetermined composition of the present invention to a subject by any suitable method.

The composition of the present invention may be administered parenterally, and preferably administered with subcutaneous infusion or topical administration (transdermal administration) via the skin, but is not limited thereto.

A suitable dose of the pharmaceutical composition may be variously prescribed by factors such as a formulation method, an administration type, age, weight, and gender of a patient, a pathological condition, food, an administration time, an administration route, an excretion rate, and response susceptibility. The oral dose of the composition of the present invention is preferably 0.1 mg/kg to 10 mg/kg (body weight) per day, more preferably 0.5 mg/kg to 1 mg/kg (body weight), but is not limited thereto. In addition, when the composition of the present invention is administered to a subject in need thereof to remove tumor-associated macrophages, the dose thereof is preferably 0.01 µg/ml to 5 µg/ml, more preferably 0.1 µg/ml to 2 µg/ml, but is not limited thereto.

The term "subject" used herein refers to all animals, such as human, monkey, dog, goat, pig or mouse, with diseases in which symptoms of various cancers or inflammatory diseases may be improved by administering the composition of the present invention. The term "phospholipase A2 (PLA2)" used herein is an enzyme functioning to generating fatty acids by hydrolyzing glycerol at the second carbon position, which catalyzes the hydrolytic activity by specifically recognizing an sn-2 acyl bond of phospholipid to release arachidonic acid and lysophospholipid. The PLA2 is commonly found even in mammalian tissues as well as bacteria, insects, and snake venom.

In one Comparative Example of the present invention, an effect of PLA2 among active ingredients of bee venom on M2-type tumor-associated macrophages was examined (Comparative Example 1). In the treatment of PLA2, it was confirmed that mRNA expression of M1 markers TNF-α and iNOS was decreased and the expression of M2 markers MMR (mannose receptor) and Arg1 was increased to promote differentiation of the M2-type tumor-associated macrophages. Therefore, it was confirmed that PLA2, which is another main ingredient, exhibits an opposite action to the melittin of the present invention as one of main peptides of the bee venom.

The present invention is to provide a method for removing tumor-associated macrophages or a method for preventing or treating tumor-associated macrophage-mediated diseases, including administering a composition including melittin or a pharmaceutically acceptable salt thereof as an active ingredient for removing tumor-associated macrophages to a subject in need thereof.

The term "therapeutically effective amount" used herein refers to an amount of melittin effective for tumor-associated macrophage-mediated diseases.

The method for preventing or treating the tumor-associated macrophage-mediated diseases of the present invention, particularly the method for preventing or treating Lewis lung cancer or inflammatory disease includes not only treating the disease itself before the development of symptoms, but also inhibiting or avoiding the symptoms thereof by administering the melittin. In the management of a disease, a preventive or therapeutic dose of a specific active ingredient will vary depending on the nature and severity of the disease or condition, and a route by which the active ingredient is administered. The dose thereof is preferably 0.1 mg/kg to 10 mg/kg (body weight) per day, more preferably 0.5 mg/kg to 1 mg/kg (body weight), but is not limited thereto. In addition, when the composition of the present invention is administered to a subject in need thereof to prevent or treat the tumor-associated macrophage-mediated diseases, the dose thereof is preferably 0.01 μg/ml to 5 μg/ml, more preferably 0.1 μg/ml to 2 μg/ml, but is not limited thereto. The administration may be administered once or several times a day. However, its dose and a dose frequency will vary depending on the age, weight and response of an individual patient, and a suitable dosage may be easily selected by those skilled in the art that naturally consider such factors.

The term "subject" used herein refers to all animals, such as human, monkey, dog, goat, pig or mouse, with diseases in which symptoms of various cancers or inflammatory diseases may be improved by administering the composition of the present invention.

In addition, the method of preventing or treating the tumor-associated macrophage-mediated diseases of the present invention may further include administering a therapeutically effective amount of an additional active agent to help in treating the diseases together with the melittin, and the additional active agent may exhibit a synergistic or auxiliary effect together with the melittin.

The present invention is to provide use of melittin or a pharmaceutically acceptable salt thereof for preparation of a pharmaceutical composition for preventing or treating tumor-associated macrophage-mediated diseases. The melittin for the preparation of the drug may be mixed with acceptable adjuvant, diluent, carrier and the like, and may be prepared as a complex preparation together with other active agents to have a synergistic action of the active ingredients.

The matters mentioned in the uses, compositions and treatment methods of the present invention are applied equally unless they contradict each other.

Advantageous Effects

According to the present invention, the composition including the melittin as the active ingredient for removing M2-type tumor-associated macrophage (TAM) selectively binds to only the M2-type tumor-associated macrophages without directly killing the cancer cells and affecting the M1-type tumor-associated macrophages to be useful for the treatment of various cancers including lung cancer as diseases associated with the M2-type tumor-associated macrophages by blocking the angiogenesis of the tumor cells.

DESCRIPTION OF DRAWINGS

FIG. 1A illustrates a result of measuring and calculating tumor sizes of a control group (CON) and a melittin-treated group (MEL) after a melittin peptide (0.5 mg/kg) is administered to tumor-resident mice every 3 days (total 5 times) from day 5 after tumor inoculation (N=5 animals per group).

FIG. 1B illustrates a Mantel-Cox survival curve (N=8 animals per group).

FIG. 1C illustrates a hematological profiling result of collecting the blood and analyzing parameters for a bone marrow function.

FIG. 1D illustrates a result of percentage (left) of neutrocytes and lymphocytes in blood leukocytes from tumor-resident mice. A neutrocyte/lymphocyte ratio (N/L ratio) was used to confirm whether acute cytotoxicity occurred as a melittin treatment result (right).

FIGS. 2A to 2B illustrate histograms after detecting a cell cycle by PI staining and gating single cells. Representative values of three replicate samples for the cell cycle were shown and peaks correspond to G1/G0, S, and G2/M stages.

FIG. 3A illustrates a result of staining splenocytes of tumor-resident mice and measuring a ratio of each immune cell in splenocytes by a flow cytometry in order to detect CD4 T cell ($CD3^+CD4^+CD8"$), CD8 T cell ($CD3^+CD8^+CD4"$), regulatory T cell (TREG; $CD4^+CD25^+Foxp3^+$), B cell (B220), regulatory B cell (BREG; $B220^+CD19^+CD25^+$), dendritic cell (DC; $CD45^+CD11b^+CD11c^+$), and macrophage (MAC; $CD45^+F4/80^+$).

In FIG. 3B, a left side illustrates an outline after marking tumor-associated macrophages (TAM) of a tumor tissue by $CD11b^+F4/80^+$ and gating $CD45^+$ cells in all survival gated cells. A right side illustrates a result of expressing percentages of $CD11b^+F4/80^+$ cell in $CD45^+$ cells by a bar graph (right).

FIG. 3C illustrates results of measuring binding of melittin to $CD4^+$, $CD8^+$ and $CD11b^+$ cells in a mixed population of splenocytes.

FIG. 3D illustrates a result of confirming whether co-staining is associated with phagocytosis by measuring the percentage of melittin$^+CD11b^+$ cells in total $CD11b^+$ cells treated with DMSO or cytochalasin D (Cyto D).

FIG. 3E illustrates a result of confirming melittin-binding subpopulations of $CD11b^+$ cells with $F4/80^+$ macrophages, $CD11c^+$ dendritic cells, and $Gr-1^+$ neutrophils according to a gating strategy.

FIG. 3F illustrates a result of confirming subpopulations of melittin-binding macrophages with $CD86^+$(M1) and $CD206^+$(M2). All plots consist of three replicate samples.

FIG. 3G illustrates a result of administering intraperitoneally chlodronate liposomes (Clo) or vehicle liposome (Con) before three days of tumor inoculation, and then treating 0.5 mg/kg of melittin every four days with Clo (Clo+Mel) (N=3 to 4 animals per group), and monitoring a tumor size for this after macrophage depletion.

FIGS. 4A and 4B illustrate results of marking M1-type tumor-associated macrophages infiltrated to tumor cells with $F4/80^+CD86^+$(top panel) and marking M2-type tumor-associated macrophages with $F4/80^+CD206^+$(lower panel).

FIGS. 4C and 4D illustrate $F4/80^+CD86^+$ and $F4/80^+CD206^+$ macrophages of splenocytes. A M1/M2 ratio was calculated based on a dot plot of $CD86^+$(M1) and $CD206^+$ (M2) cells in $F4/80^+$ macrophages. All plots were gated on $CD45^+$ cells of total surviving gated cells.

FIG. 5A illustrates qPCR results of M2 phenotypic markers (Vegf, Mrc1/CD206, 11-10 and Tgf-β) and an M1 phenotypic marker (Tnf-α) in bone marrow-derived macrophages (BMDM). Cells were stimulated with LPS or IL-4 for 24 hours and cultured for another 24 hours in the presence of PBS or melittin. An increase in folding of each gene is a result of normalization to a level of an unstimulated group (indexed as untreated).

FIG. 5B illustrates a result of comparing relative mRNA levels of Vegf and flt1/VEGFR1 from melittin-treated tumor cells with a PBS-treated control group and showing the result in fold-difference.

FIG. 5C illustrates a result of measuring TNF-α, IL-10 and TGF-β production in a supernatant of a bone marrow-derived macrophage culture using ELISA.

FIGS. 5D and 5E illustrate results of measuring VEGF and CD206 expression by Western blot analysis. β-actin was used as a loading control group and a representative blot of 4 to 5 experiments was shown. The unmarked data did not show a significant (ns) difference compared to the CON group.

FIGS. 6A and 6B illustrate results of measuring intracellular ROS production by H2DCFDA staining in unstimulated cells (untreated) or M1-differentiated macrophages treated with PBS (CON) or melittin (MEL), respectively.

FIG. 6C illustrates a result of measuring a relative phagocytic index of melittin or cytochalasin D (cytoD)-treated bone marrow-derived macrophages compared to a control group by an internalized latex-bead fluorescence intensity.

FIG. 7A illustrates a result of visualizing VEGF (red) by immunofluorescence staining in paraffin sliced tumors. Nuclei were counterstained with DAPI (blue).

FIG. 7B illustrates a result of visualizing CD31 (green) positive cells by immunofluorescence staining in paraffin sliced tumors. Nuclei were counterstained with DAPI (blue).

FIG. 7C illustrates a result of quantifying the intensity of VEGF by image J.

FIG. 7D illustrates a result of quantifying the intensity of CD31 by image J. Data were expressed as mean±SEM.

BEST MODE OF THE INVENTION

Hereinafter, the present invention will be described in more detail by the following Examples. However, the following Examples are just illustrative of the present invention and the scope of the present invention is not limited thereto.

Example 1. Preparation of Experimental Materials 1-1. Animals and Cells

Wild-type C57BL/6 mice were purchased from SLC Japan Bred. Co., Ltd. (Shizuoka, Japan). This study was approved by the Kyung Hee Medical Center Institutional Animal Care Committee. All animals were maintained in a light/dark cycle of 12 hours in a pathogen-free environment and taken in with food and water.

LLC, MLE12, A549 and H441 cells were cultured in a medium (LLC, DMEM, MLE12, DMEM/F-12, A549 and H441, RPMI-1640, Welgene, Gyeongsan, Korea) added with 10% heat-inactivated fetal bovine serum (FBS, Welgene), 100 U/ml penicillin, and 100 μg/ml of streptomycin (Invitrogen Life Technologies, Rockville, Md., USA). The cells were cultured every 2 to 3 days until 80% confluent. In all experiments, the cells were cultured at 37° C. with 95% humidity and 5% $CO_2$.

1-2. Preparation of Bone Marrow-Derived Macrophage (BMDM)

Cells were harvested as previously described to generate mouse bone marrow-derived macrophages. The cells were cultured for 7 days in an RPMI-1640 complete culture medium containing 10 ng/ml of mouse recombinant M-CSF (R & D systems, Minneapolis, Minn., USA). After the cells were differentiated into M0 macrophages, the cells were smeared in a 6-well plate ($1 \times 10^6$ cells/well) and cultured overnight under 100 ng/ml LPS or 20 ng/ml mouse recombinant IL-4 (R & D system) to induce differentiation of M1 or M2 phenotype macrophages.

Example 2. Statistical Significance Evaluation Method

Statistical significance was evaluated by a Student's t-test for single comparison using Prism 5.01 software (GraphPad Software Inc., San Diego, Calif., USA) or a Tukey's post-hoc test for multiple comparison following one-way ANOVA.

Example 3. Suppression of Tumor Growth and Increased Survival Rate of Melittin—In Vivo 3-1. Blood Cell Profile Test The blood was collected from the retro-orbital plexus of mice under anesthesia. The blood was immediately mixed with EDTA and analyzed by a Hemavet 950 auto-sampler (Drew scientific, Waterbury, Conn., USA) according to manufacturer's instructions. The parameters of leukocytes, erythrocytes, and platelets were measured and expressed as a percentage.

3-2. Experiment Results

In order to confirm a tumor growth suppressing effect of melittin, cancer cells were injected subcutaneously into C57BL/6 mice, and 0.5 mg/kg of melittin peptide or PBS was administered by intraperitoneal injection every two days. A cancer growth rate in the control group was fast, but the cancer growth in the melittin-treated group was late.

Figure 1A:
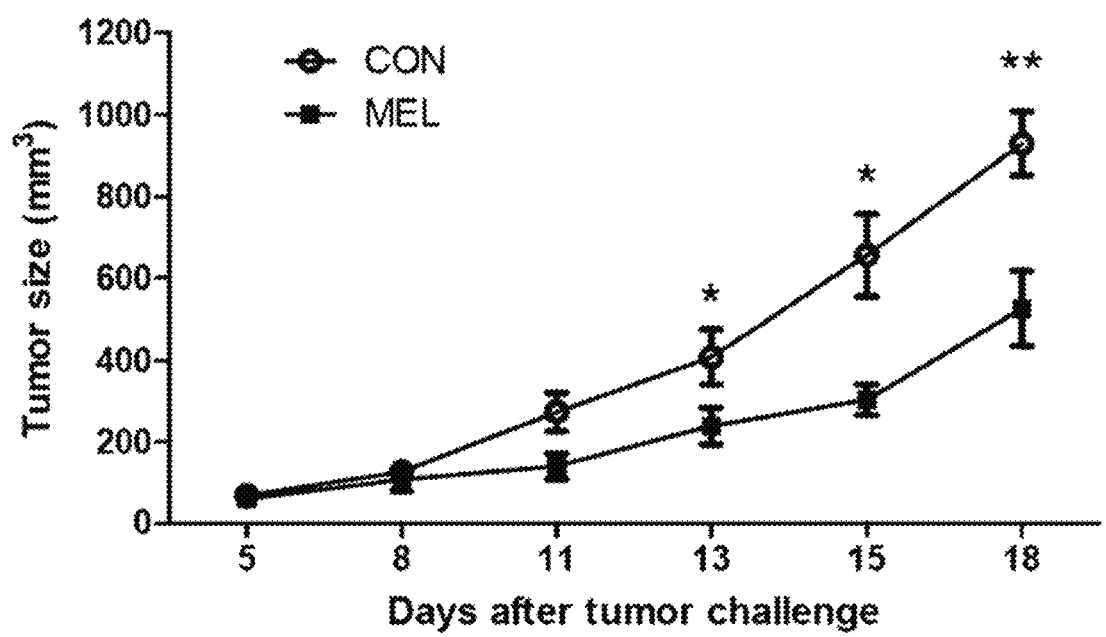
FIGS. 1A-1D illustrates an anti-cancer effect of melittin in vivo. All data were expressed as mean±SEM ($*P<0.05$, $**P<0.01$).
Figure 1B:
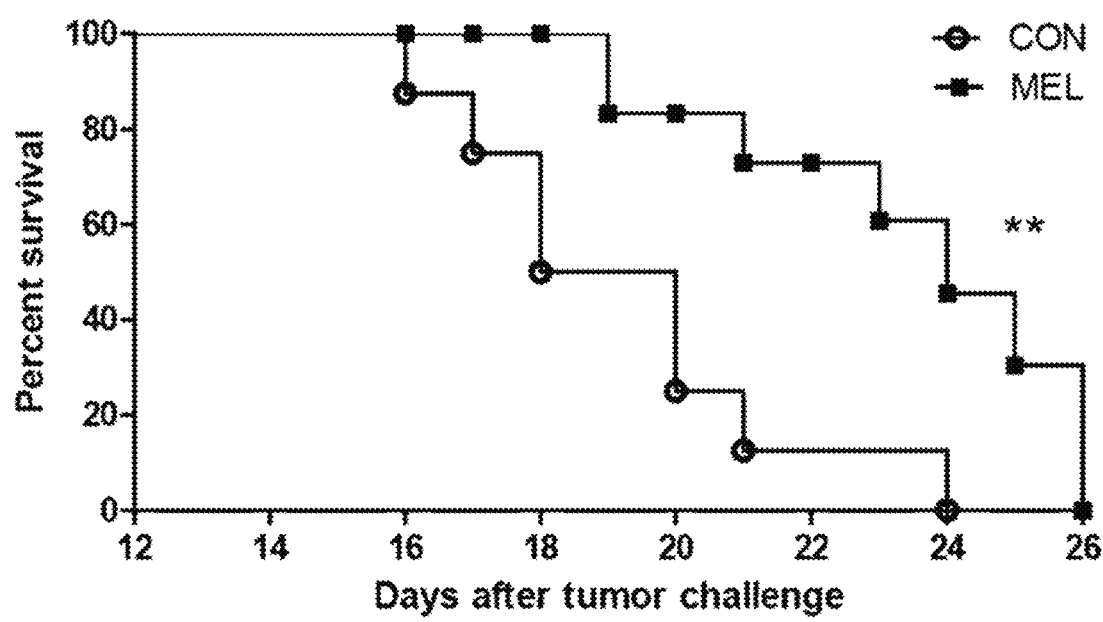

After 13 days of administration, the cancer growth of the melittin-treated group was markedly reduced by 40% compared to the control group and suppressed by about 45% on day 15 (FIG. 1A). In addition, in the melittin-treated group, it was confirmed that the survival period was significantly longer than that of the control group (PBS-treated group) by Mantel-Cox analysis. Therefore, it was confirmed that the melittin was able to delay the growth of cancer to extend the survival period of the existing cells.

The weights of mice were measured every 2 to 3 days until 0 to 18 days. There was no weight loss in the control group and melittin-treated groups (control group on day 0: 22.44±0.37 and control group on day 18: 23.6±0.30; melittin-treated group on day 0: 22.84±0.36 and melittin-treated group on day 18: 24.72±0.45).

Figure 1C:
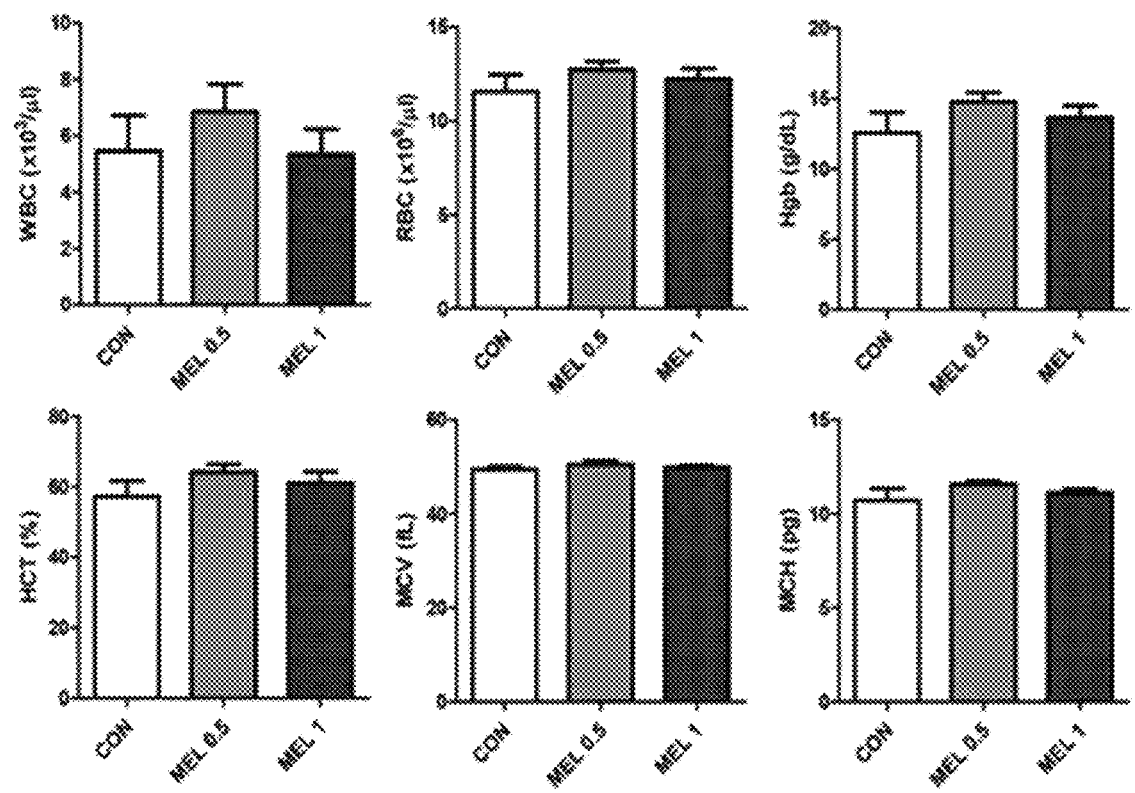
Figure 1D:
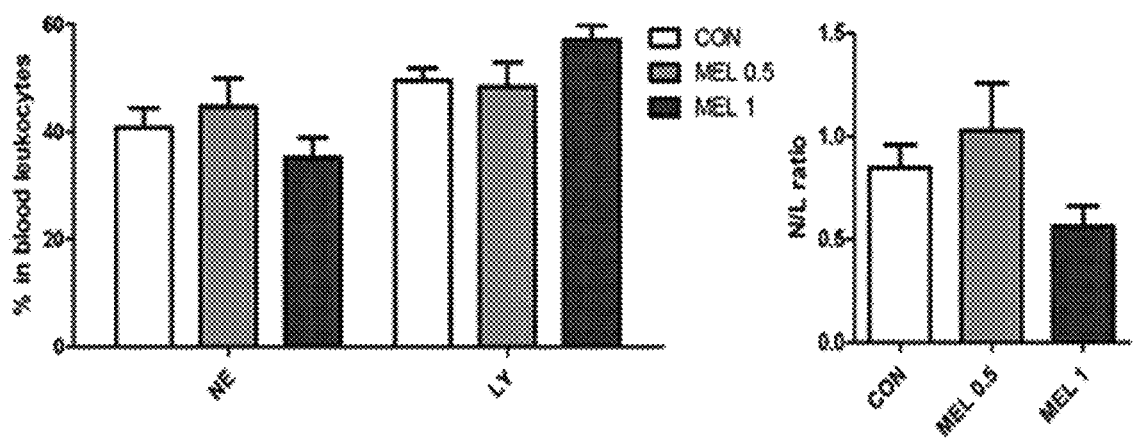

In order to confirm the side-effects of the bone marrow function of melittin, hematological profiling was performed. The blood was collected via the retro-orbital plexus during anesthesia. 0.5 mg/kg or 1 mg/kg melittin treatment did not result in significant changes in hematological factors (WBC, RBC, Hgb, HCT, MCV and MCH) (FIG. 1C). Moreover, it was suggested that no significant change in neutrophils, lymphocytes, and a neutrophil-lymphocyte ratio (N/L ratio) was caused, and the melittin does not cause acute cytotoxic damage (FIG. 1D).

Example 4. Confirmation of Direct Killing Effect of Melittin on Cancer Cells—In Vitro

4-1. Cell Cycle Analysis

Briefly, cells were smeared in a 6-well plate at a density of $5 \times 10^5$/well and cultured for 24 hours with 0.1, 0.5, 1, and 2 μg/ml of PBS or melittin. The cells were collected, washed twice with PBS, fixed with 70% pre-cooled ethanol and stored at −20° C. overnight. The cells were washed and resuspended in PBS 500 μl containing 0.1% Triton X-100 and RNase 20 μg/ml. Next, 50 μg/ml of propidium iodide (PI) was added. Stained cells were cultured at 37° C. for 20 minutes and then detected by a FACS Calibur flow cytometer (Becton Dickinson, San Jose, Calif., USA). Data were analyzed by Flow Jo software (Treestar, Inc., San Carlos, Calif., USA).

4-2. Cell Separation and Flow Cytometry Analysis

A tissue was dissociated by cutting the tumor into thin pieces and gently stirring in DNase I (1 U/ml; Roche, Indianapolis, trypsin-EDTA (Gibco)) under DMEM (Welgene) preheated at 37° C. for 1 hour. The tissue was mechanically dissociated in a 100 μm nylon mesh strainer, then single cells passed through a 40 μm nylon mesh strainer, and the spleen was mechanically dissociated with a 40 μm nylon mesh strainer. RBC was dissolved for 5 minutes in a 1× pharmlyse buffer.

The cells were stained with fluorescent tag antibodies. All data were detected by a FACS Calibur flow cytometer and analyzed with FlowJo software. CD45-FITC, CD3-FITC, CD4-PE, CD4-FITC, CD8-APC, CD11b-APC, CD11 c-PE, CD25 (CD12-FITC)-PE, CD25-APC, B220-FITC, CD19-PE, CD86-APC, and Foxp3-Alexa Fluor647 were purchased from BD bioscience and F4/80-PE and CD206-APC were purchased from Biolegend (San Diego, Calif., USA).

4-3. Experimental Results

Figure 2A:
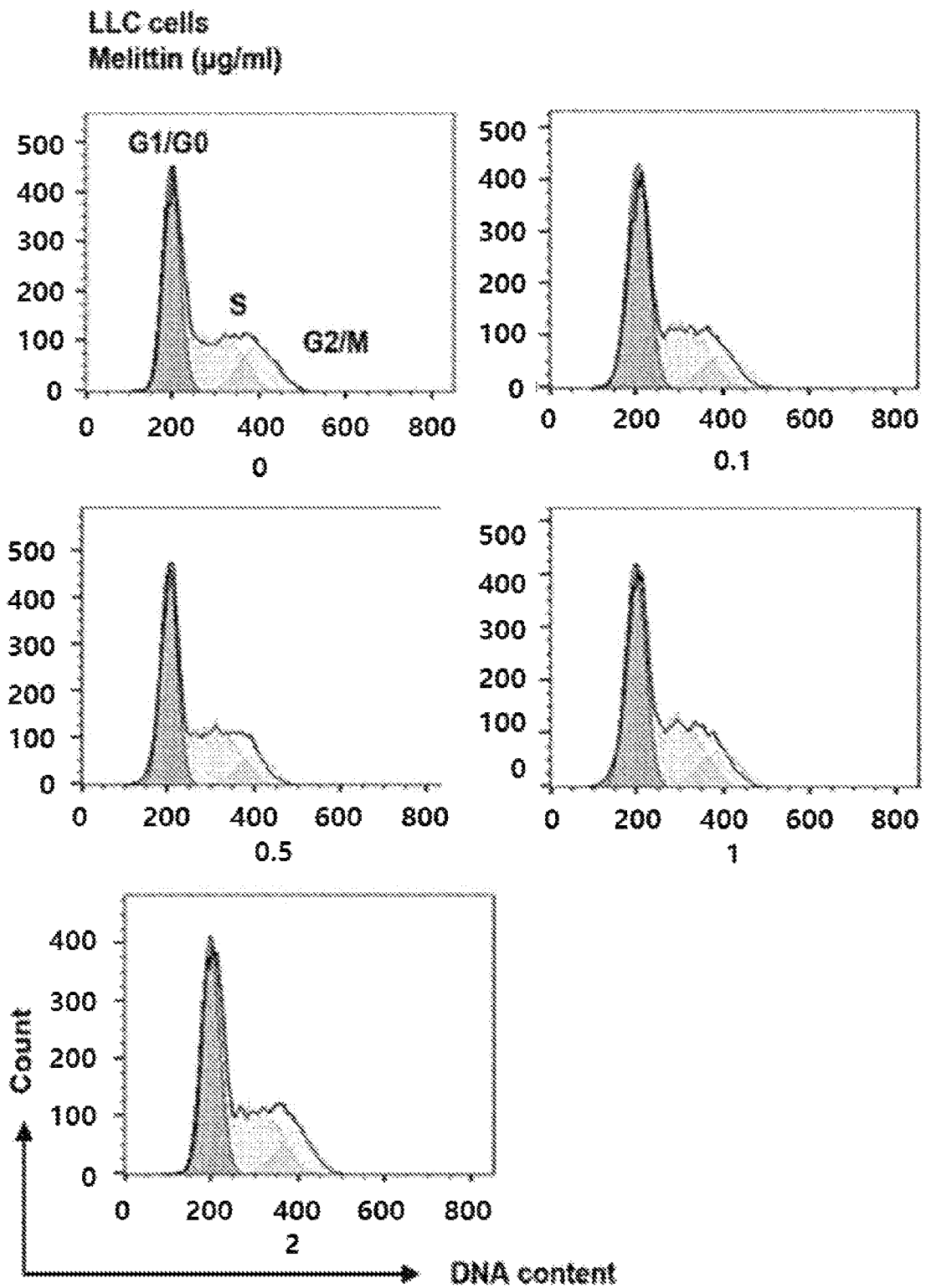
FIGS. 2A-2B illustrate confirming an effect of melittin on a cell cycle of tumor cells in vitro. Results were expressed as mean±SEM ($*P<0.05$, $P<0.01$, $*P<0.001$).
Figure 2B:
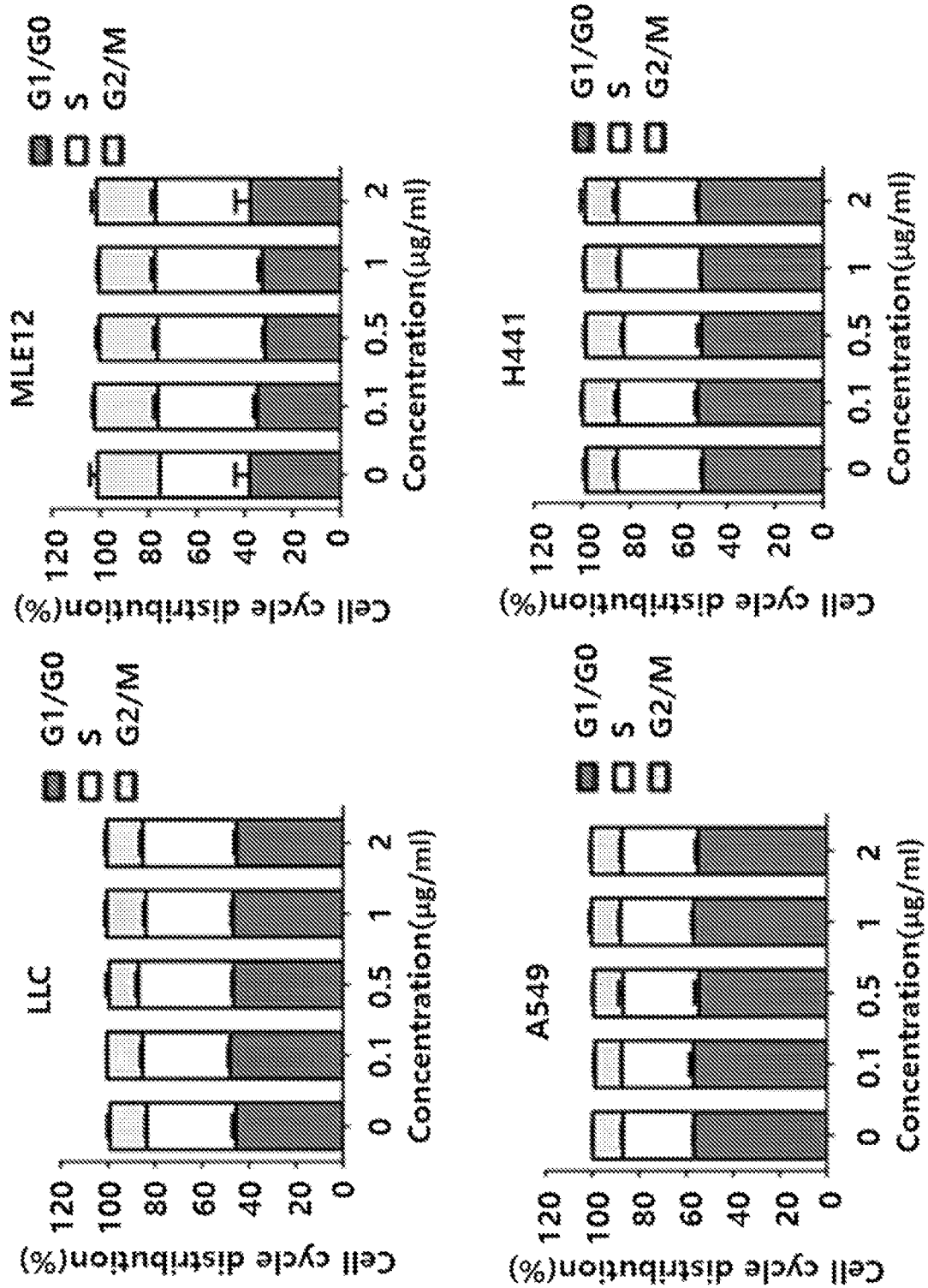

In PI-stained lung cancer cells, an effect of melittin on the cell cycle of cancer cells was confirmed by flow cytometry. There was no percentage change at each stage (FIG. 2) and the results show that 0.1 to 2 μg/mL of melittin dose not affect the cell cycle of tumor cells. Accordingly, it can be seen that there is no direct killing effect on cancer cells.

Example 5. Effect of Melittin Treatment on Macrophage Number in Tumor Microenvironment—In Vivo

5-1. Tumor Cell Challenge

Lewis lung carcinoma cells were mixed with a Matrigel matrix (Coming, N.Y., USA) to generate a tumor model. Male C57BL/6 wild-type mice (6 to 8 weeks old) were inoculated subcutaneously in the right flank with $5 \times 10^4$ cells per mouse. After 5 days of tumor injection, recombinant melittin (GenScript Corporation, Piscataway, N.J., USA) was administered intraperitoneally every three days (total 5 times). Before 3 days of tumor injection, macrophage deficiency was performed by clodronate liposomes (first dose of 200 μl per mouse, maintenance dose of 100 μl intraperitoneally every 4 days). Clodronate liposome and control liposome were purchased from FormuMax (Sunnyvale, Calif., USA). A tumor size was monitored every 2 to 3 days by measuring two opposite diameters (volume=length×width×width/2). If the tumor size exceeded 5% of the body weight, the mice were sacrificed for a next experiment set. Thereafter, the tumor and the spleen were surgically removed.

5-2. Experimental Results

It was tested whether melittin treatment caused a change in the number of immune cells. Screening of the immune cells was performed by flow cytometry on $CD4^+$ T cells, $CD8^+$ T cells, B cells, dendritic cells, and macrophages from splenocytes of mice with cancer. The flow cytometry was performed in the same manner as Example 3-2.

Figure 3A:
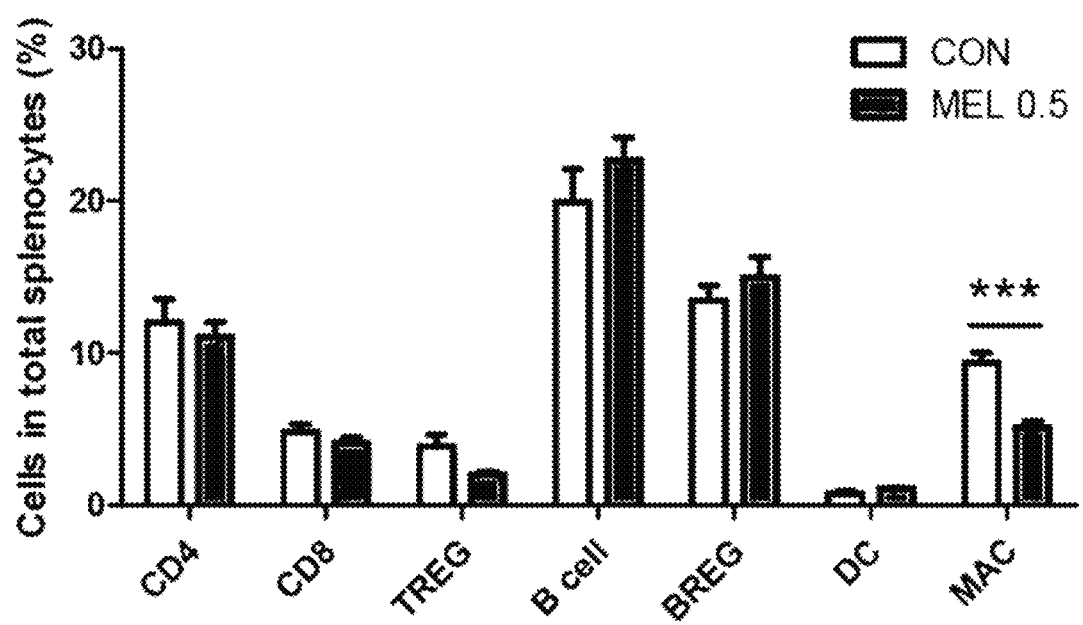
FIGS. 3A-3G illustrates an effect of selectively reducing tumor-associated macrophages in treatment with melittin to tumor cells. All values were expressed as mean±SEM ($P<0.01$, $*P<0.001$).

The melittin significantly reduced only $CD45^+F480^+$ macrophages (9.05±in control group vs. 5.10±0.42 in melittin-treated group). The number of regulatory T cells also decreased slightly, but it was not a significant change. There was no percentage change of other immune cells from total splenocytes in the control and melittin-treated groups (FIG. 3A).

Figure 3B:
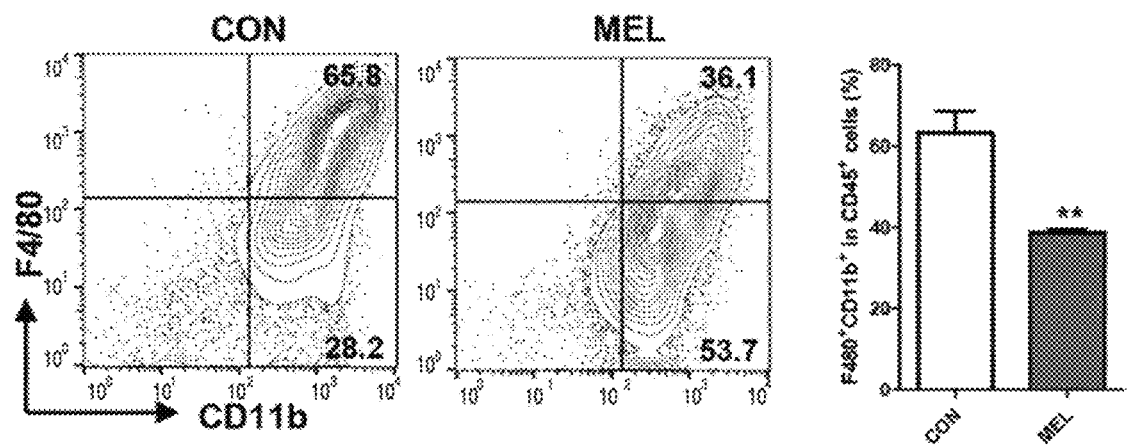
Figure 3C:
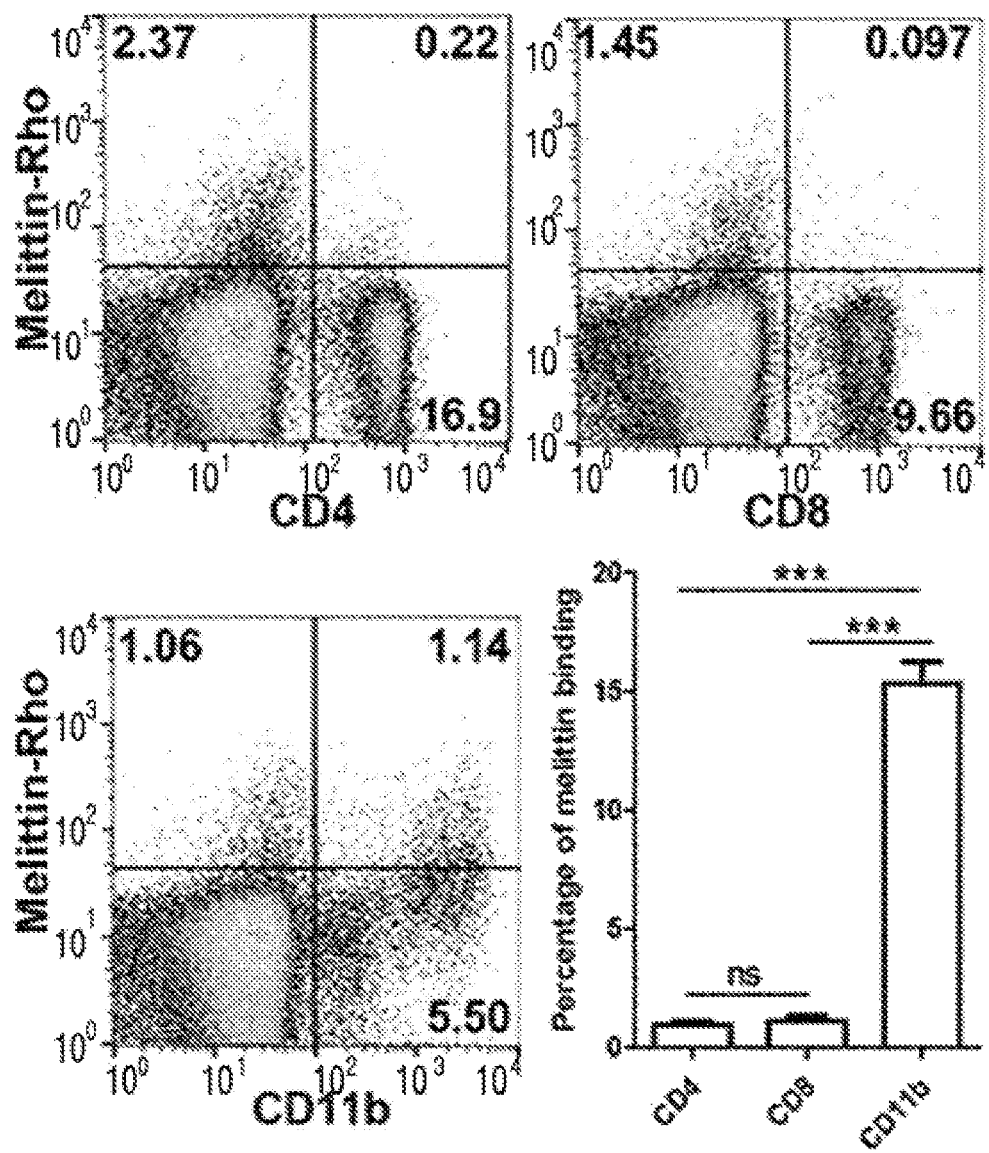
Figure 3D:
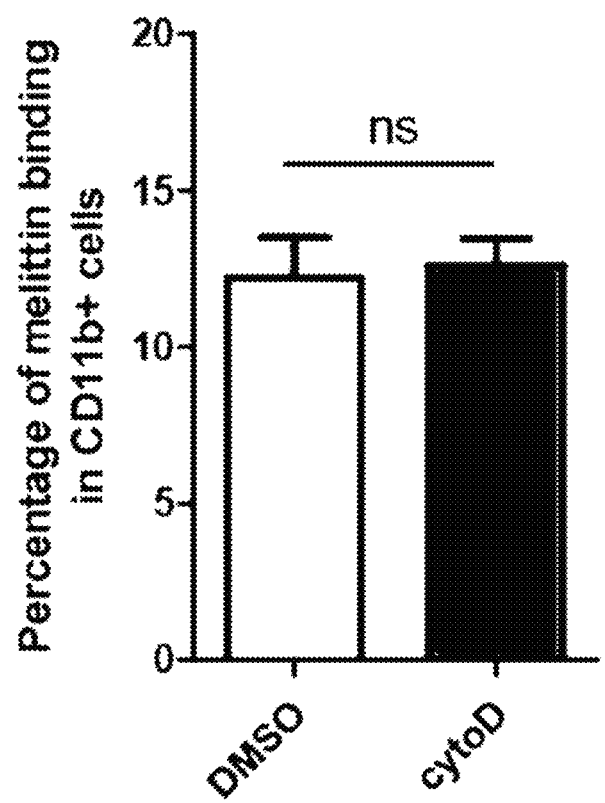
Figure 3E:
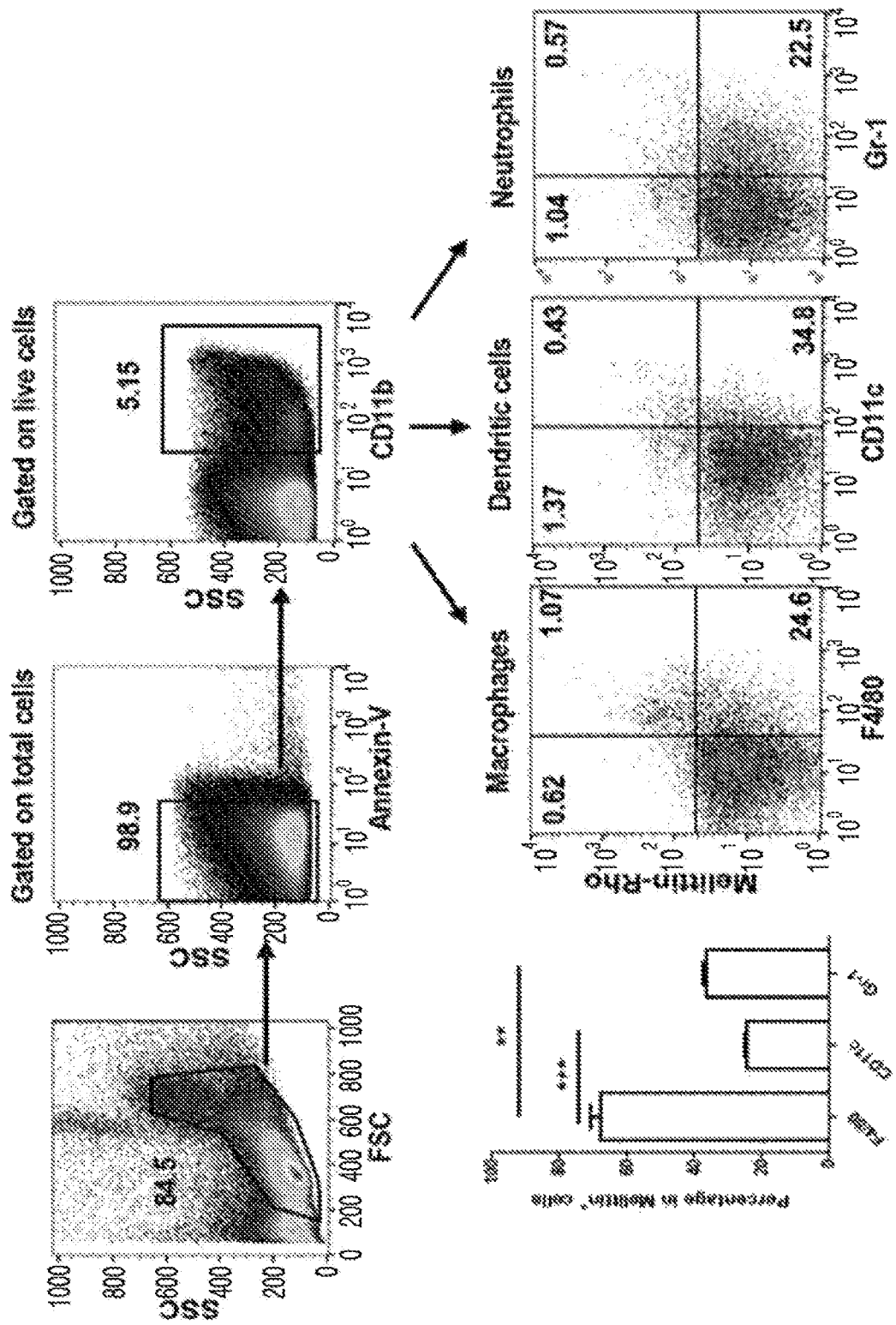
Figure 3F:
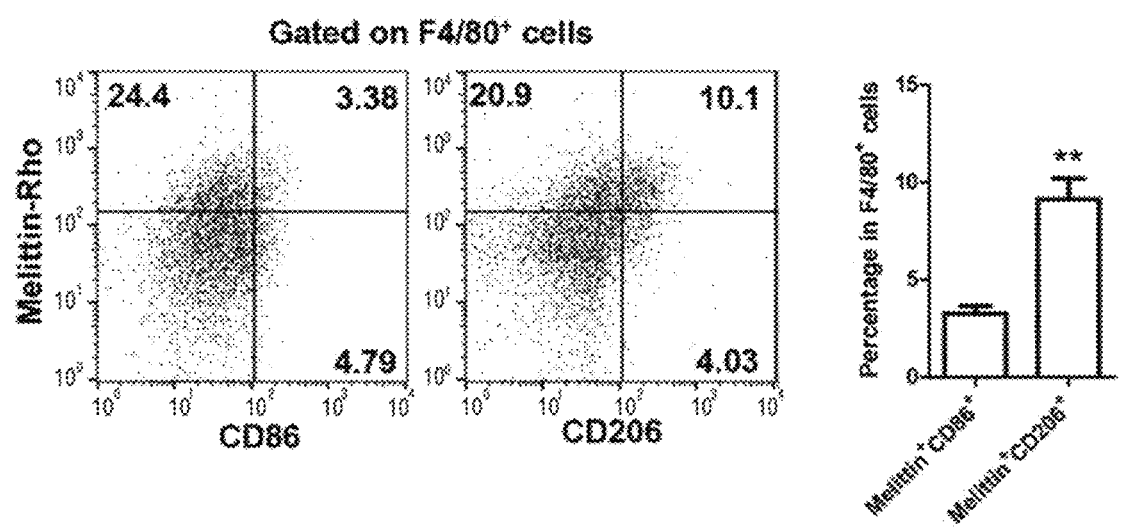
Figure 3G:
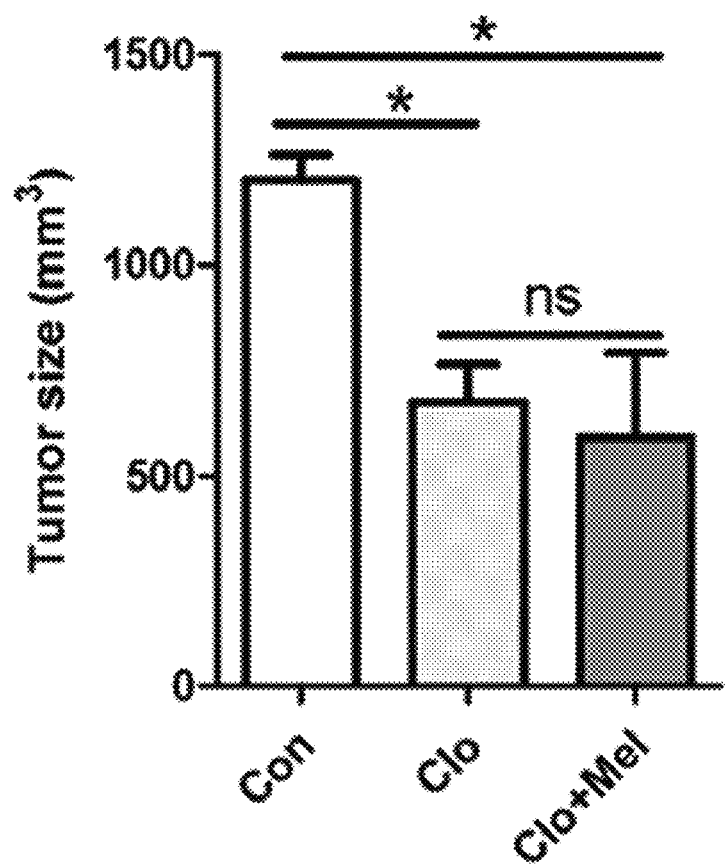

The effect of melittin on tumor-associated macrophages (TAM) was confirmed. In melittin treatment, the percentage of $CD11b^+F4/80^+$ macrophages in $CD45^+$ tumor-infiltrating leukocytes was significantly reduced (63.25±5.34 in control group vs. 38.70±0.79 in melittin) (FIG. 3B). Macrophages were depleted with clodronate liposomes to confirm whether the role of melittin in controlling tumor-associated macrophages is associated with tumor growth suppression. As expected, the depletion of macrophages by clodronate significantly reduced the tumor growth compared to the control group. In treatment of melittin together with clodronate, the tumor growth is not additionally suppressed, indicating that the tumor suppressing effect of melittin is closely associated with tumor-associated macrophages (FIG. 3G). Therefore, it was confirmed that melittin acts specifically on tumor-associated macrophages among various immune cells ($CD4^+$, $CD8^+$, B cells, etc.), and controls the number of immune cells to exhibit a tumor growth suppressing effect.

Example 6. Confirmation of Selectivity of Melittin Peptide for M2-Type Tumor-Associated Macrophage—In Vitro

6-1. Study on Melittin Binding

Rhodamine-binding melittin peptides were purchased from GenScript (Piscataway, N.J., USA). Splenocytes were smeared in a 6-well culture plate containing 0.5 μg/ml of rhodamine-binding melittin. After 1 hour, cells were harvested and the non-binding peptides were washed twice. The cells were stained with APC-binding antibodies for 1 hour at 4° C. and it was confirmed that melittin binds to CD4$^+$ and CD8$^+$ T cells and CD11 b$^+$ monocytes.

Splenocytes were pretreated with 10 nM cytochalasin D or vehicle (DMSO) in a 37° C. incubator for 1 hour to confirm whether the binding of melittin to CD11b$^+$ cells was associated with phagocytosis. Next, the cells were cultured with rhodamine-bound peptides and stained with CD11b-APC antibodies as described above.

To observe the binding of melittin to CD11b$^+$ subpopulations in splenocytes, macrophages, dendritic cells, and neutrophils, anti-mouse F4/80-FITC, CD11c-APCcy7, and Gr1-PEcy7 (e-bioscience) were examined. Annexin-V was added to a sample before data collection to distinguish dead cells. M1 of the M2-type tumor-associated macrophage was stained with CD86-PEcy7 (e-bioscience) or CD206-PercpCy5.5 (Biolegend). The cells were detected in FACS Calibur or FACS CantoII.

6-2. Experimental Results

A binding test was performed to determine whether melittin may selectively bind to CD11b$^+$. Splenocytes were cultured with rhodamine-bound melittin peptides and stained with CD4, CD8 and CD11b antibodies. Melittin binding was approximately 16% in CD11b$^+$ cells and 1% in CD4$^+$ or CD8$^+$ cells (FIG. 3C). To confirm that the detection of peptides in CD11b$^+$ cells was associated with phagocytosis, before splenocytes were treated with melittin, 10 nM cytochalasin D (Cyto D) and an actin polymerization inhibitor were pretreated to suppress phagocytosis. The amount of melittin$^+$CD11b$^+$ double positive cells in the total CD11b$^+$ cell population had no difference in a DMSO control group and a Cyto D-treated groups. Therefore, it may be confirmed that the melittin has affinity for CD11b$^+$ cells, and this affinity was not associated with phagocytosis.

Next, the melittin binding subpopulations of CD11b$^+$ cells were examined by staining F4/80, CD11c, and Gr-1 with respect to macrophages, DC, and neutrophils, respectively. The melittin was preferentially bound to macrophages (67.70±2.96 in annexinli-CD11b$^+$ melittin$^+$ cells), while low binding to DC (24.44±0.56) and neutrophils (36.36±0.95) was shown (FIG. 3E). Furthermore, it was confirmed that the melittin was preferentially bound to the M2-type tumor-associated macrophages. To confirm phenotypes of the melittin-bound macrophages, M1 type was marked as CD86 and M2 type was marked as CD206. In F4/80$^+$ cells, the percentage of the melittin and CD206 double positive population (9.15±1.05) was significantly higher than the percentage of the melittin$^+$CD86$^+$ population (3.27±0.39) (FIG. 3F). Therefore, it was confirmed that the melittin had the affinity with the tumor-associated macrophages regardless of phagocytosis, and was specifically bound to the M2-type tumor-associated macrophages.

Example 7. Effect of Melittin on M1/M2-Type Ratio

Figure 4A:
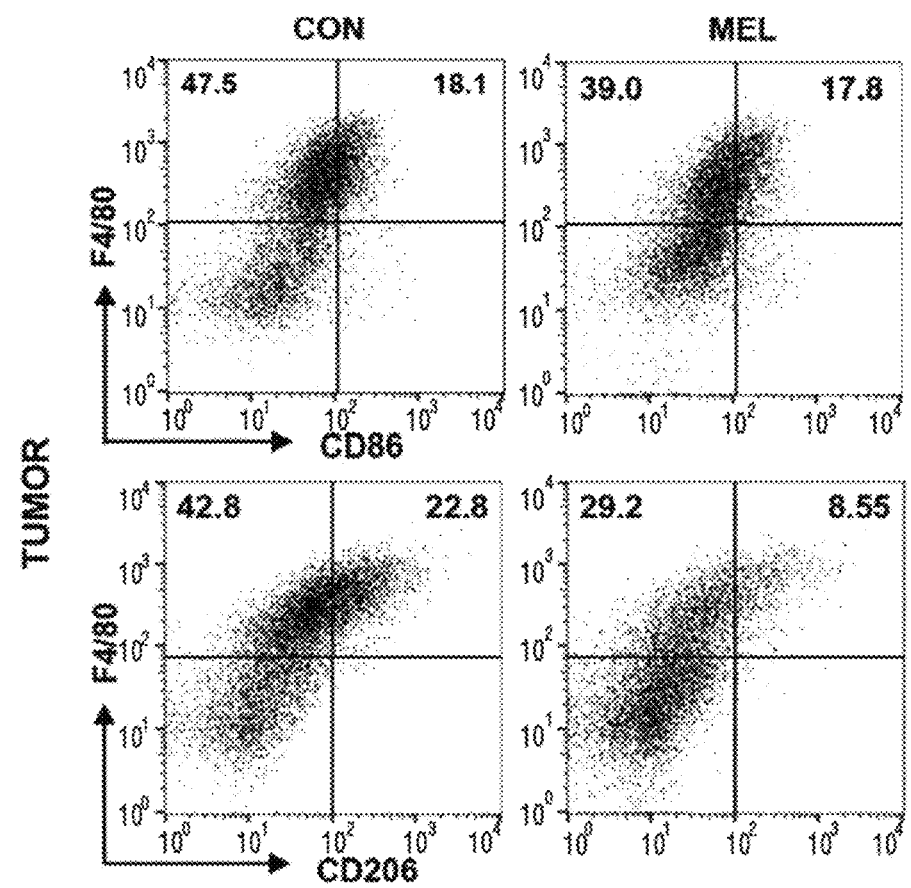
FIGS. 4A-4D illustrates improvement of a M1/M2 ratio due to the reduction of M2-type $CD260^+$tumor-associated macrophages in tumor cells in vivo. Values were expressed as mean±SEM ($**P<0.01$).
Figure 4B:
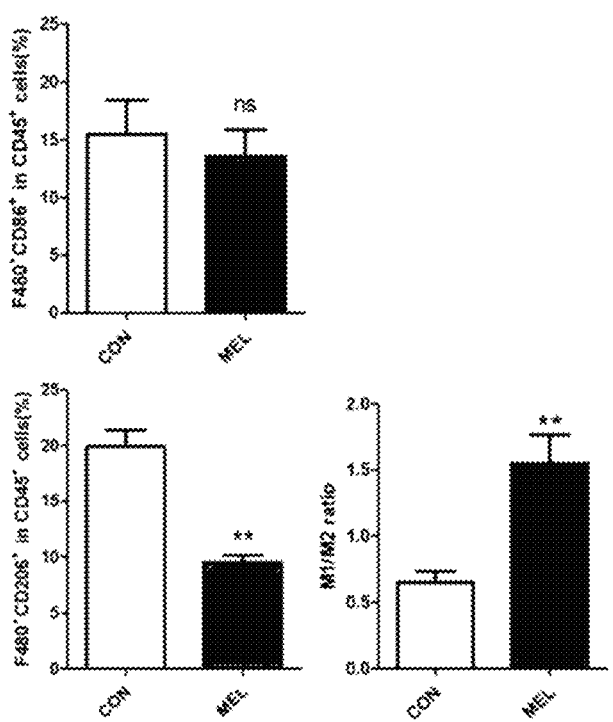
Figure 4C:
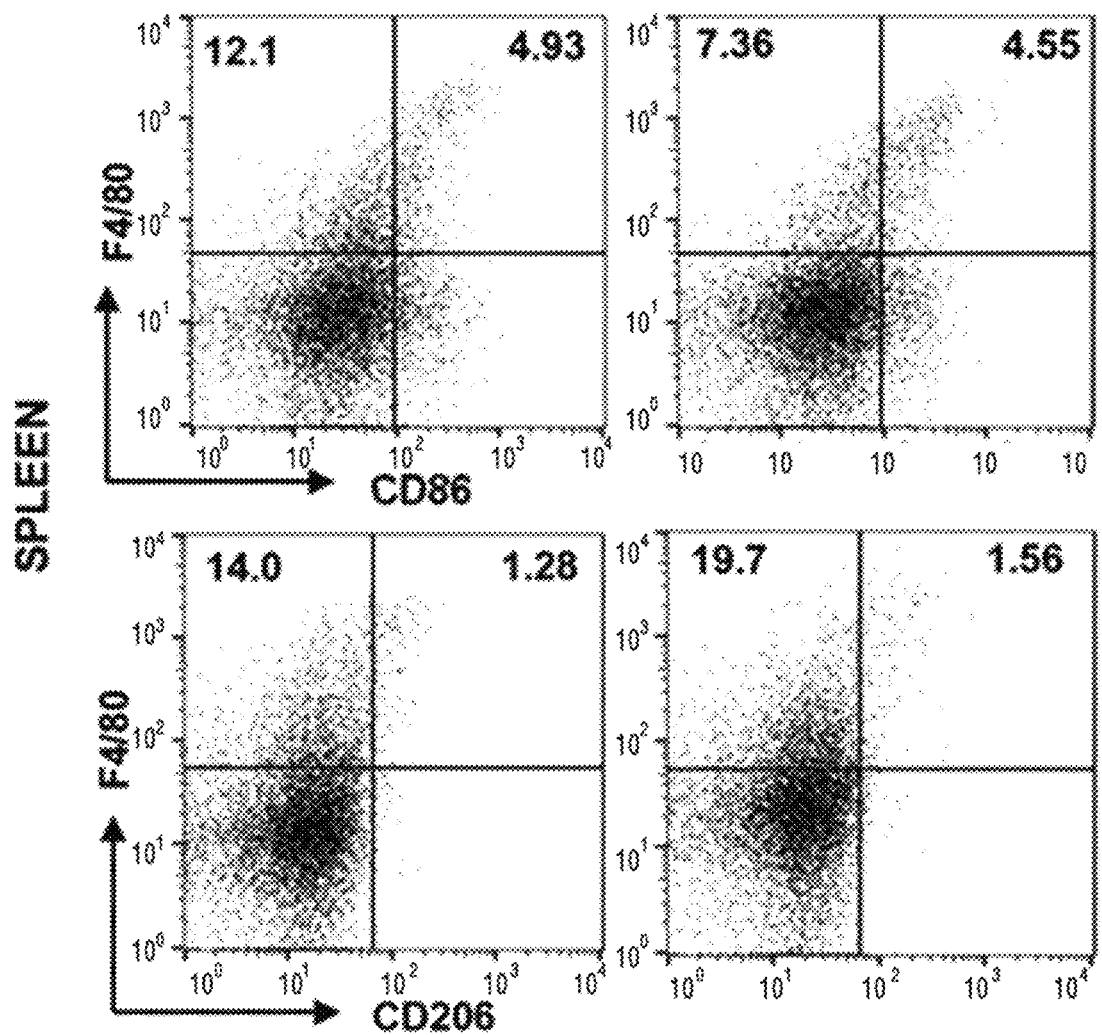
Figure 4D:
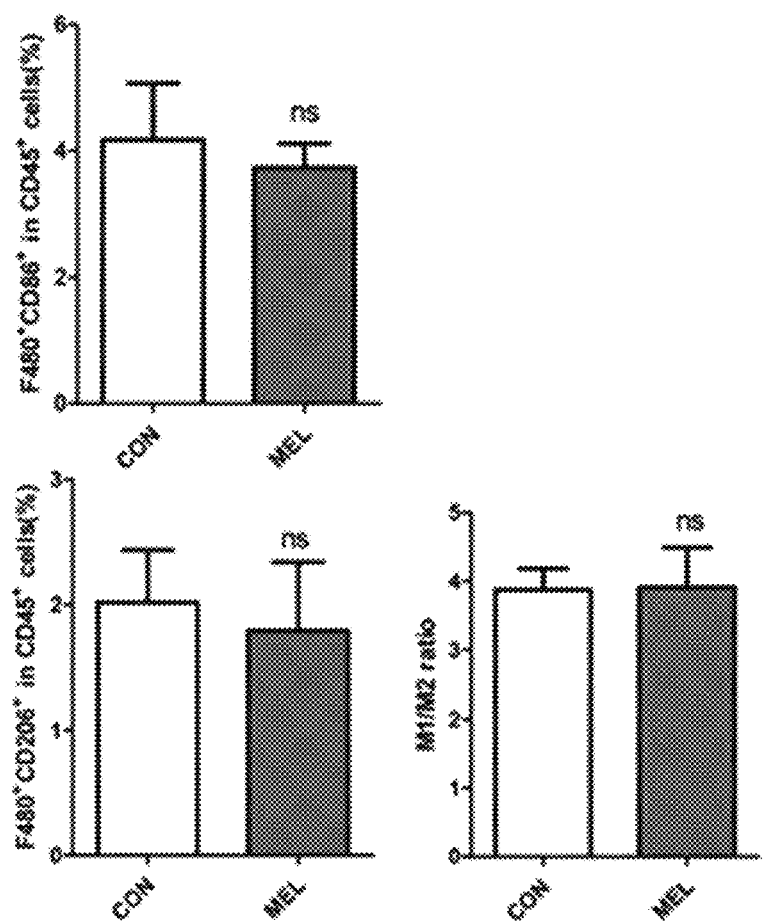

Although M1-type and M2-type tumor-associated macrophages are present in the tumor tissue, tumor-promoting tumor-associated macrophages are considered to be M2-type phenotypes. Some studies have found that as the M1/M2 ratio is increased, the survival rate in a human cancer model is improved. Although the number of F4/80$^+$CD86$^+$ was not increased in CD45$^+$ cells, the percentage of F4/80$^+$CD206$^+$ in CD45$^+$ cells was significantly reduced from the control group (19.90±1.49) to the melittin-treated group (9.53±0.63) (FIGS. 4A and 4B). Surprisingly, the level of M1 or M2 type macrophages in splenocytes was not changed by melittin treatment (FIGS. 4C and 4B). As a result, the M1/M2 ratio of tumor cells was significantly increased in the melittin-treated group (M1/M2=0.65 control group vs. M1/M2=1.55 melittin-injected group) (FIG. 4B, right panel). However, in the spleen, the ratio (approximately 3.9) was not changed but maintained (FIG. 4D, right panel). Through these results, it may be confirmed that the melittin may specifically reduce the M2-type tumor-associated macrophages as a therapeutic indicator and significantly increase the M1/M2 ratio without affecting M1-type or other macrophages remaining in the spleen.

Example 8. Effect of Melittin on M2-Type Tumor-Associated Macrophages

8-1. Quantitative Real-Time PCR

Total RNA was extracted and reverse-transcribed into cDNA from 1×10$^6$ Lewis lung carcinoma cells or bone marrow-derived macrophages treated with melittin or PBS. Quantitative real time PCR was performed according to previous reports. Data were expressed as 2-ΔΔσ for experimental genes, normalized to GAPDH, and expressed as a fold change compared to an LPS or IL-4 untreated control group. The following primers were used: Gapdh(for: ACCCAGAAGACTGTGGATGG (SEC) ID NO: 1); rev: CACATTGGGGGTAGGAACAC (SEQ ID NO: 2)), Tnf-α (for: TTCTG TCTACTGAACTTCGGGGTGATCGGTCC (SEQ ID NO: 3); rev: GTAT GAGA-TAGCAAATCGGCTGACGGTGTGGG (SEQ ID NO: 4), Mrc1/CD206(for: AGTGGCAGGTGGCTTATG (SEQ ID NO: 5); rev: GGTT CAGGAGTTGTTGTG (SEQ ID NO: 6)), Il-10(for: ATAACTGCAC CCACTTCCCA (SEQ ID NO: 7); rev: TCATTTCCGATAAGGCTTGG (SEQ ID NO: 8)), Tgf-β(for: GAAGGCAGAGTTCAGGGTCTT (SEQ ID NO: 9); rev: GGTTCCTGTCTTTGTGGTGAA (SEQ ID NO: 10)), Vegf(for: GGAGA TCCTTCGAGGAGCACTT (SEQ ID NO: 11); rev: GGCGATTTAGCAG CAGA-TATAAGAA(SEQ ID NO: 12)), Flt1/VEGFR1(for: ACAT-TGGTGGTGGCTGACTCTC (SEQ. ID NO: 13); rev: CCTCTCCTT CGGCTGGCATC (SEQ ID NO: 14)).

8-2. Western Blot Analysis

Total proteins were extracted using a RIPA buffer from melittin or PBS treated-bone marrow-derived macrophages and quantified by Bio-Rad analysis. 20 μg of protein was isolated on an 8% SDS Tris-glycine gel and transferred to a nitro cellulose cell membrane (Invitrogen). The following antibodies and dilution factors were used: VEGF goat polyclonal antibody (sc-1836, 1:1000, Santa Cruz), actin goat polyclonal antibody (sc-1616, 1:1000, Santa Cruz), rabbit anti-mouse CD206 (MCA2235GA 1:200, AbD serotec), anti-goat IgG conjugated to HRP (SA007, 1:1000, GenDE-POT), and anti-rat IgG bound to HRP (405405, 1:1000, Biolegend). Protein bands were visualized using an ECL solution (GE healthcare) and measured with Image J software. The strength of the protein has been normalized above that of actin.

8-3. Confirmation of Reactive Oxygen Species (ROS)

Bone marrow-derived macrophages were smeared in a 24-well plate and treated with melittin or PBS for 24 hours.

The cells were added with 5 μM C2',7'-dichlorodihydrofluorescein diacetate (H2DCFDA; molecular probe) and cultured at 37° C. for 30 minutes. The H2DCFDA-containing medium was removed and the cells were washed twice with preheated PBS. After the cells were collected, ROS production levels were immediately analyzed using flow cytometry.

8-4. Phagocytosis Assay

Cells were smeared in a 96-assay well plate and treated as described above. The cells were pretreated for 30 minutes with or without cytochalasin D before treatment with latex bead-FITC (Sigma-Aldrich). After 2 hours of incubation, the cells were washed with PBS three times to remove foreign particles. Fluorescence of internalized beads was measured using emission of 527 nm after excitation of 485 nm in a fluorescent plate reader (Fluorskan Ascent FL) quenching with trypan blue.

8-5. ELISA

The secretion of cytokine from the culture medium was analyzed using an ELISA kit according to a procedure recommended by a provider. Mouse IL-10 and
TNF-α were purchased from BD Biosciences, and TGF-β was purchased from R & D systems. Results were expressed as pg of normalized cytokine per mg of total protein.

8-6. Experimental Results

Figure 5A:
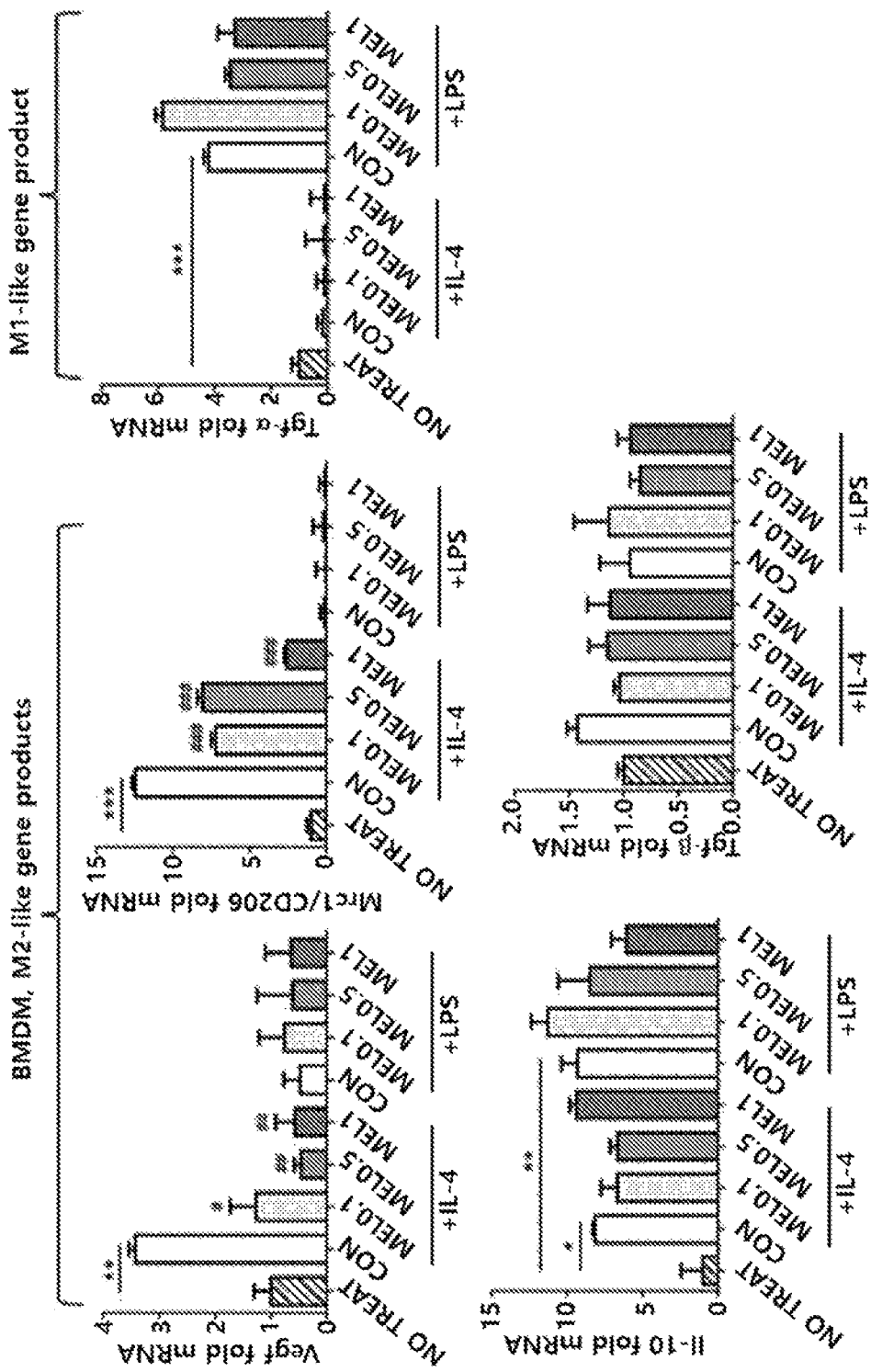
FIGS. 5A-5E illustrates an effect of regulating CD206 and VEGF expression by melittin in M2-type tumor-associated macrophages in vitro. Values are mean and error bars represent SEM. *P<0.05, P<0.01, and *P<0.001 indicate significant differences between an LPS or IL-4-treated CON group and a non-treated group. #P<0.05, ##P<0.01, ###P<0.001 indicate significant differences between a melittin-treated group and a CON group. Data were expressed as mean±SEM.
Figure 5B:
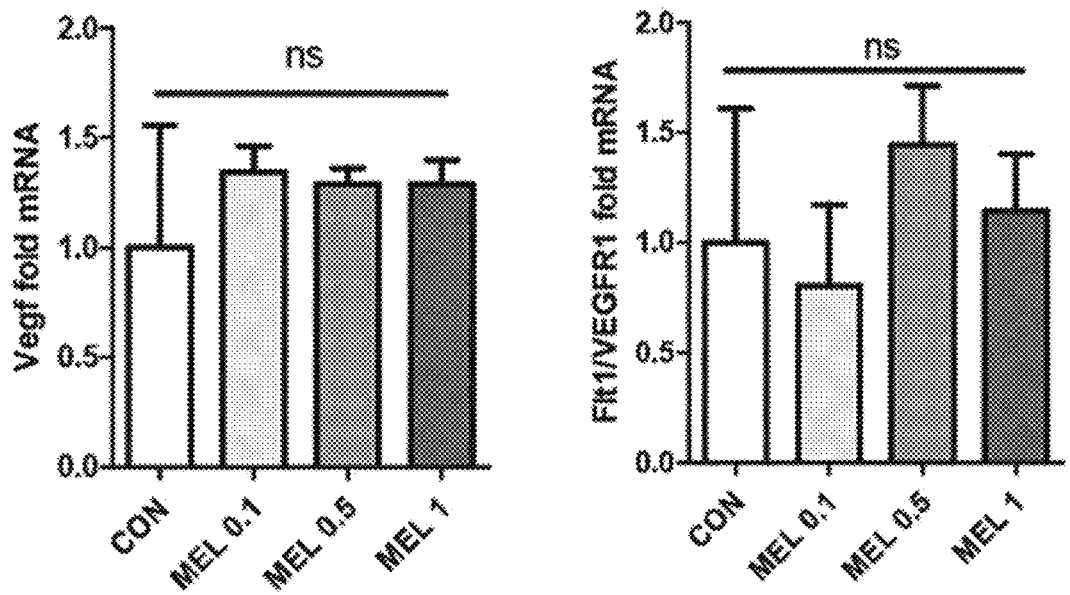
Figure 5C:
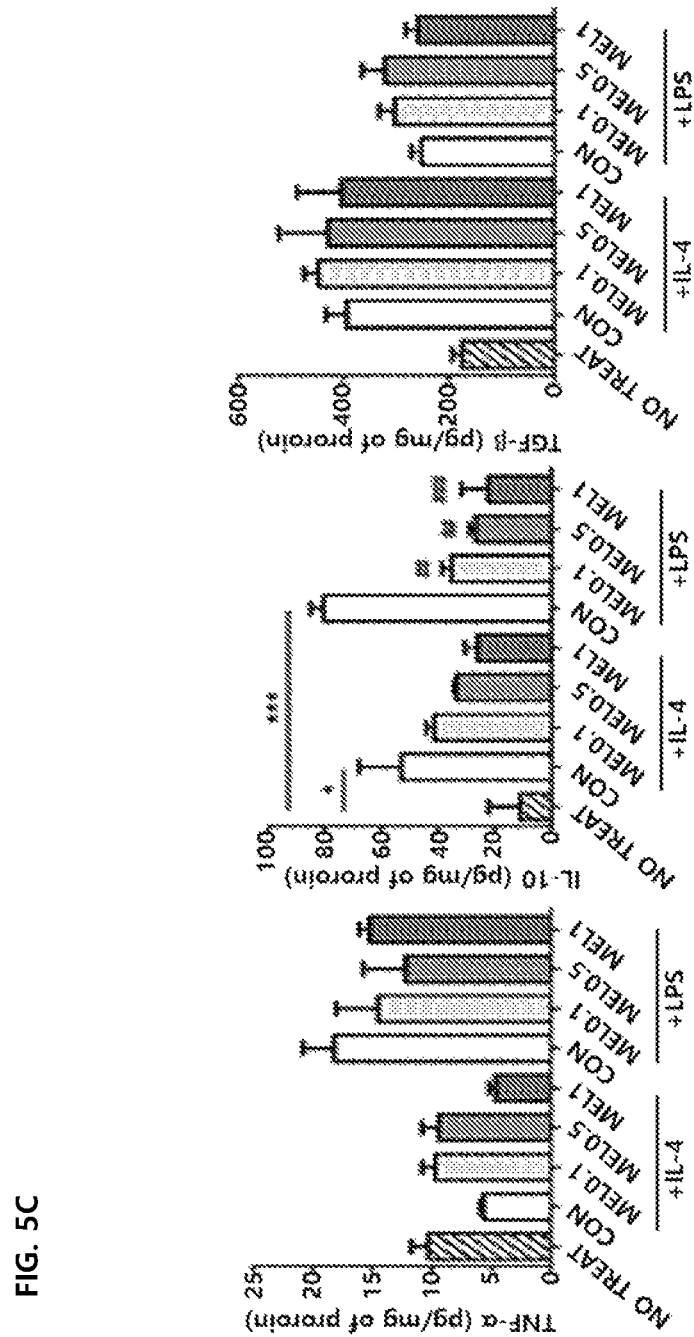
Figure 5D:
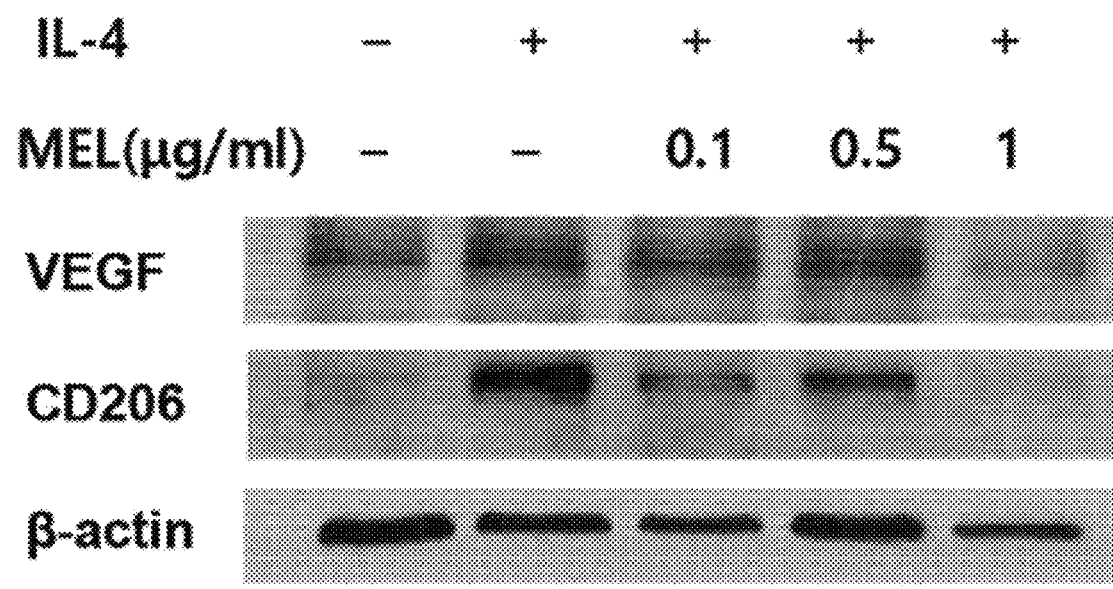
Figure 5E:
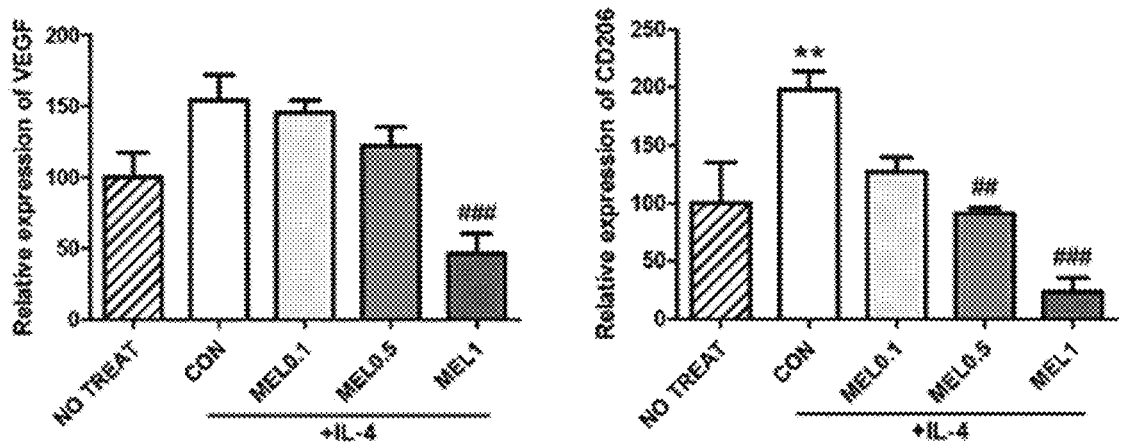

In order to measure whether the melittin may change the macrophage M1/M2 ratio, quantitative real-time PCR was performed. Bone marrow-derived macrophages (BMDM) were stimulated with LPS or IL-4 and cultured under melittin or PBS. Whole cell lysates and culture supernatants were analyzed by expression of mRNA and protein. The gene/protein level of TNF-α of an inflammation-induced marker was increased by LPS stimulation, but the melittin treatment did not affect the expression of M2-associated angiogenesis-promoting markers VEGF, CD206, TFG-β and IL-10, and after 4 stimulation, IL-10 was increased. However, the gene/protein expression levels of TGF-β and IL-10 in M2-type bone marrow-derived macrophages were not changed by melittin treatment (FIGS. 5A and 5B). Significantly, melittin-treated-M2-type bone marrow-derived macrophages showed significantly reduced mRNA levels for Vegf and Mrc1/Cd206 compared to the control group (FIG. 5A). The expression levels of VEGF and CD206 proteins reduced by melittin were further confirmed by Western blot (FIGS. 5D and 5E). Next, the mRNA levels of Vegf and flt1/VFGFR were examined in Lewis lung carcinoma cells. The mRNA levels had no large difference in control and melittin-treated groups (FIG. 5B). Through these results, it may be confirmed that the melittin reduces only expression of M2 genes such as (Mrc1/CD205 and Vegf) and does not alter the expression of M1 genes such as Vegf and flt1NEGFR in Lewis lung carcinoma cells, and thus the melittin has a potential anti-angiogenic effect by the reduced M2 gene expression.

Figure 6A:
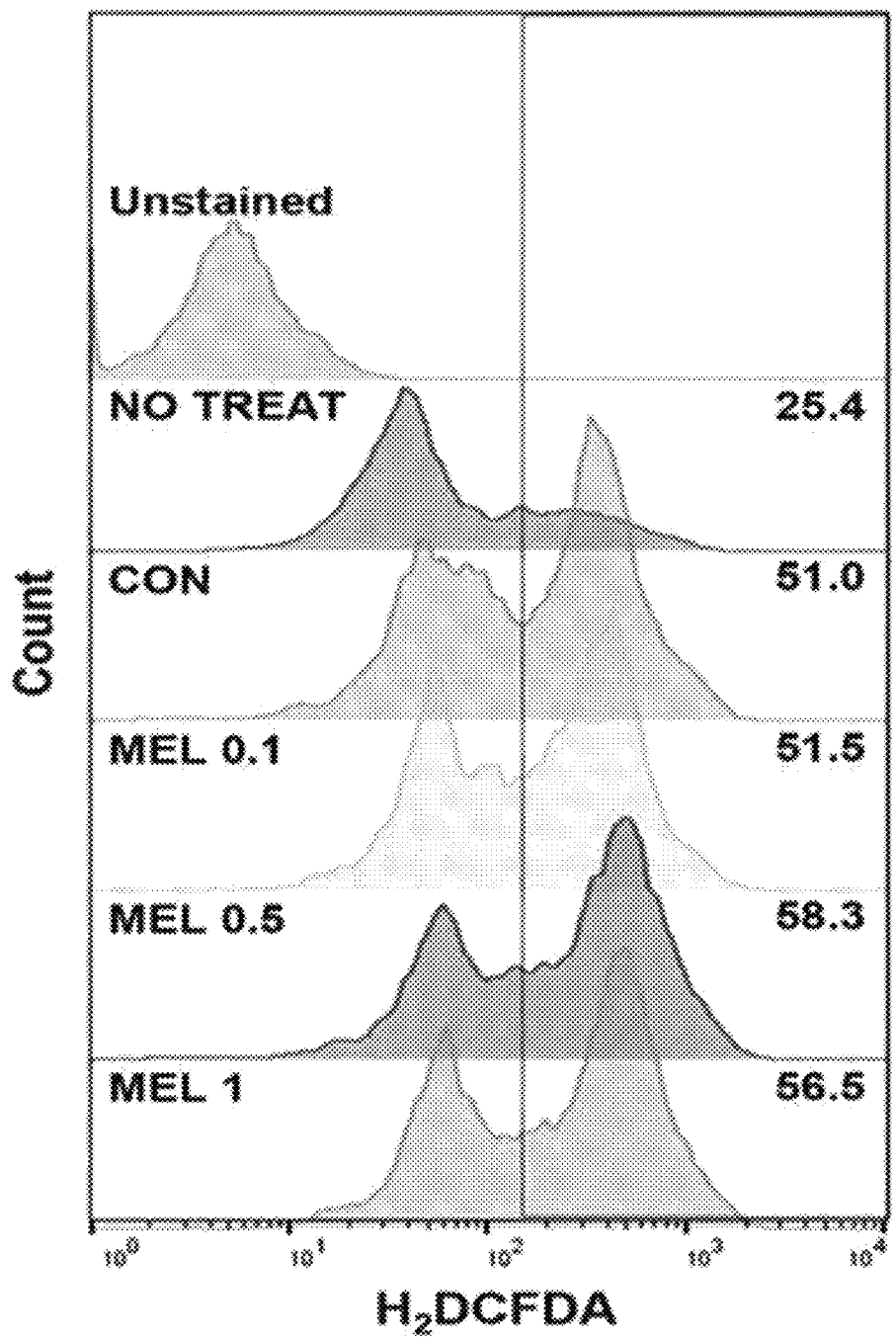
FIGS. 6A-6C illustrates an effect of melittin on macrophage function. Mean±SEM for three replicate samples was shown (*P<0.05, ***P<0.0001).
Figure 6B:
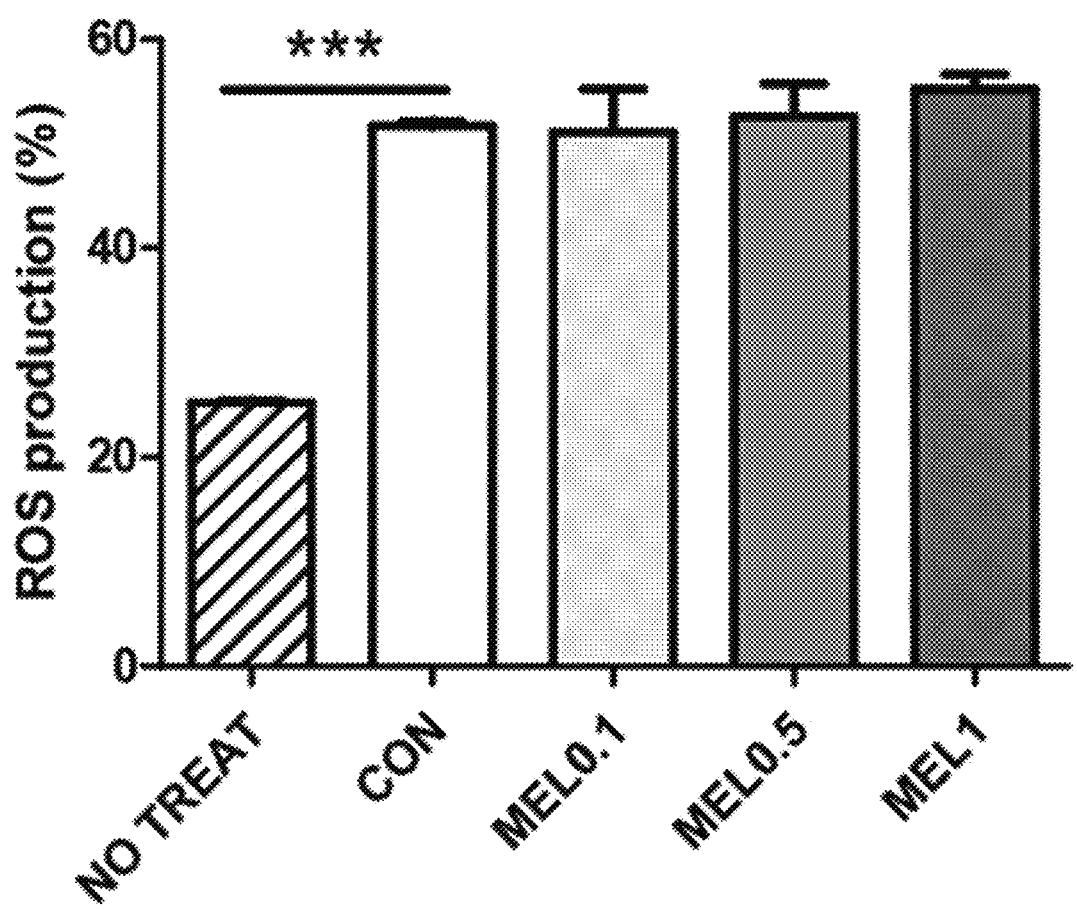
Figure 6C:
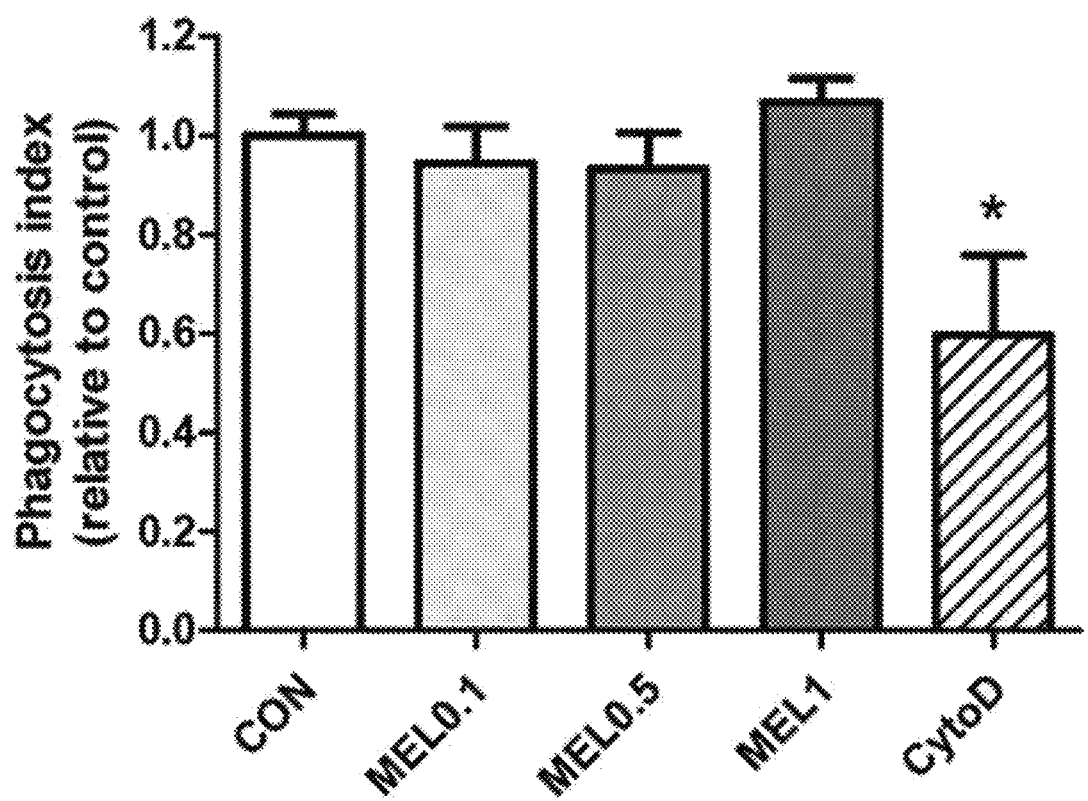

Inflammation-induced M1-type tumor-associated macrophages are required to have functional properties such as phagocytosis, endocytosis, cytokine secretion, and ROS production to help in killing pathogens. The effect of melittin on macrophage functions was confirmed by measuring the ROS production and phagocytosis index of M1-type bone marrow-derived macrophages. Intracellular ROS levels had no difference in a melittin-treated bone marrow-derived macrophage group and a control bone marrow-derived macrophage group (FIGS. 6A and 6B). Phagocytic capacity was not changed by melittin treatment, but the phagocytosis index was significantly lowered in a cytochalasin D-treated group as an actin polymerization inhibitor (FIG. 6C). Through these results, it was confirmed that the melittin treatment does not suppress the functional properties of the macrophages, such as ROS production and phagocytosis.

Example 9. Top-down Control Effect of Selective CD206$^+$ Tumor-associated Macrophages

9-1. Tissue Preparation and Immunofluorescence Confocal Microscopy Analysis

The tumor of inoculated mice was fixed overnight with paraformaldehyde, dehydrated, and then placed in paraffin. Slices (5 μm thick) of the inserted tissue were cut in a rotary microtome and deparaffinized. The antigens of the slides were recovered by an autoclave in a trisodium citrate buffer (pH 6) for 1 minute, washed with PBS and then blocked for 1 hour with 1.5% BSA containing 0.2% Triton X-100. The slides were cultured overnight at 4° C. with anti-VEGF and anti-CD31 primary antibodies (1:200, Santa Cruz Biotechnology, Santa Cruz, Calif., USA).

All tissue slices were cultured at room temperature for 1 hour and then visualized with an alexa-488 or alexa-594 conjugated secondary antibody (1:500, Invitrogen). All the antibodies were diluted with a 0.5% BSA solution and cultured in a wet chamber. The slides were fixed with a DAPI solution and analyzed by laser scanning confocal microscopy (Bio-Rad, Richmond, Calif., USA). All images were captured with LSM and total integration density was measured with image J software.

9-2. Experiment Results

The tumor-associated macrophages promote tumor angiogenesis by secreting various growth factors, vasculogenesis-promoting factors, and cytokines that stimulate the vasculogenesis and tumor growth. VEGF considered as the strongest angiogenic protein not only induces angiogenesis, but also maintains the survival of new blood vessels in the tumor by stimulating endothelial sprouting. CD31 (PE-CAM) is a vascular marker and has been widely used to detect the angiogenesis in a tumor mouse model. Therefore, two major angiogenic markers, VEGF and CD31 were used to confirm an effect of melittin on angiogenesis suppression.

Figure 7A:
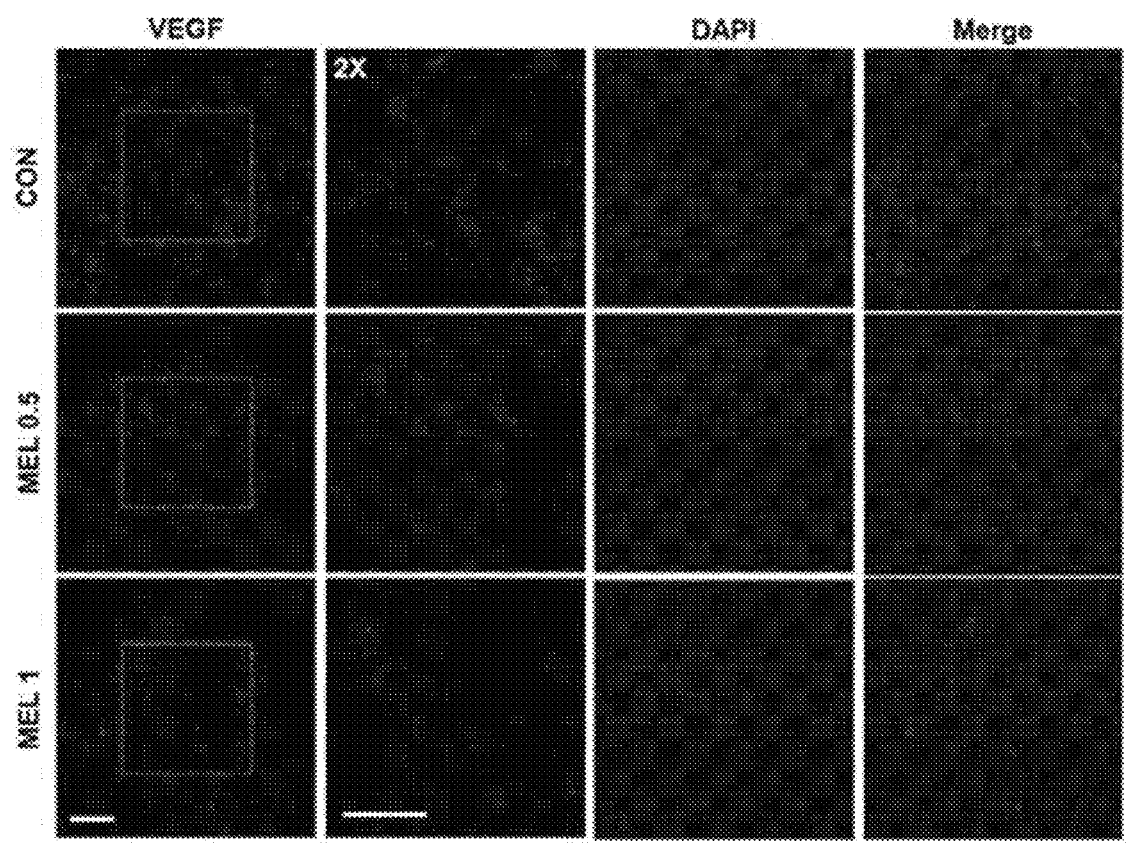
FIGS. 7A-7D illustrates confirming an effect of melittin treatment on a tumor angiogenesis network. Data were expressed as mean±SEM (P<0.01 compared to corresponding control group, *P<0.001, total magnification, 400×, scale bar, 50).
Figure 7B:
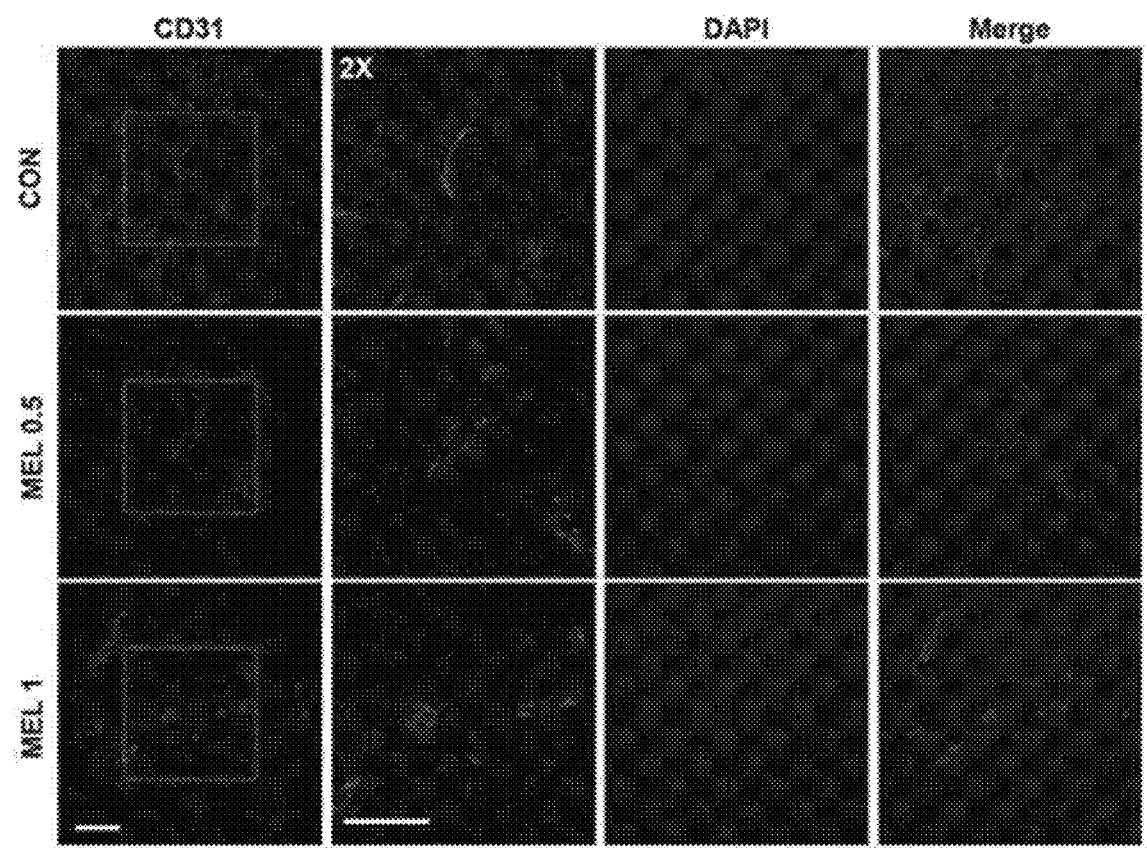
Figure 7C:
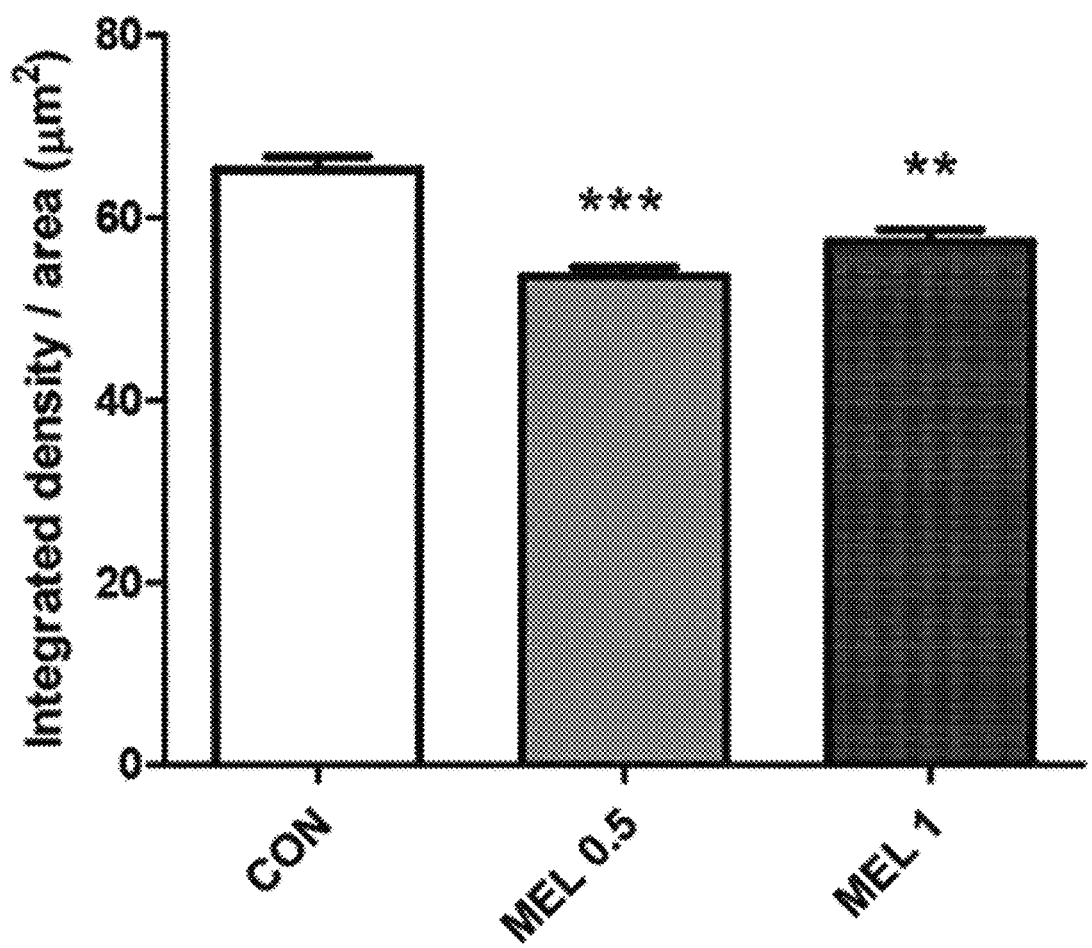
Figure 7D:
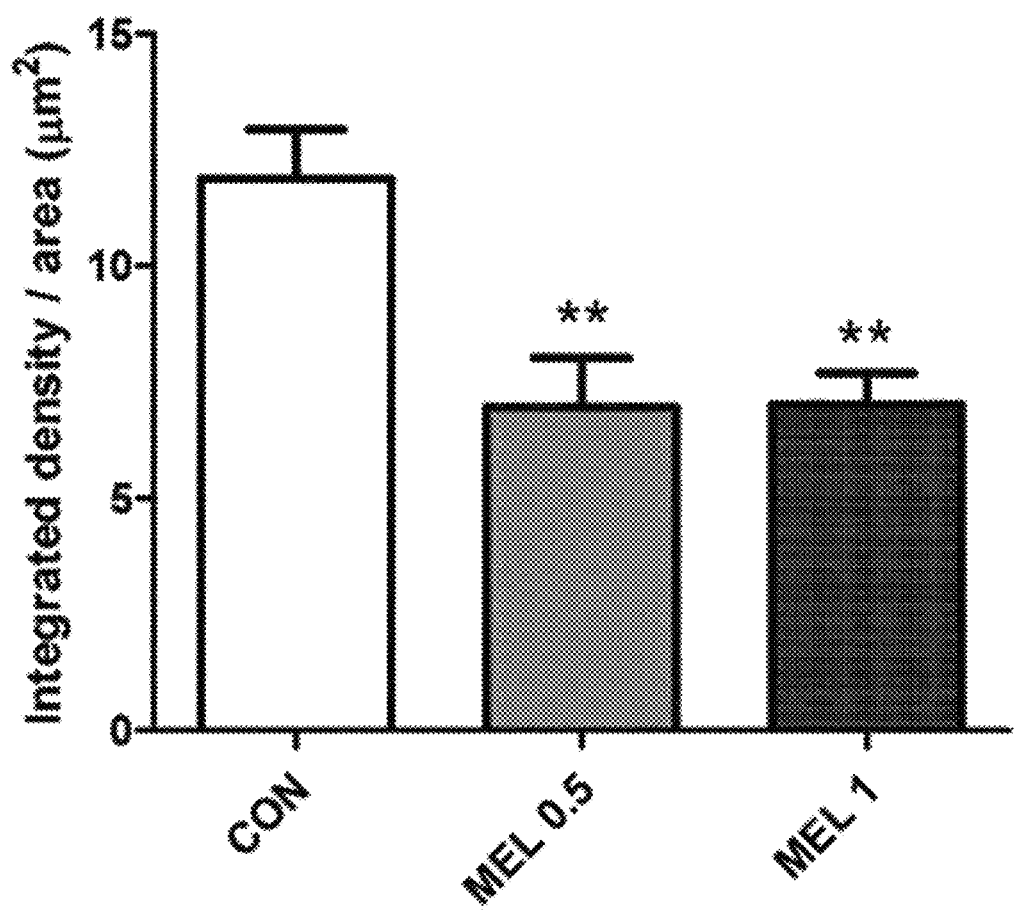

Immunofluorescence staining showed a decrease in levels of VEGF and CD31 in a melittin-treated tumor tissue compared to a PBS group (FIGS. 7A and 7B). The integrated density was measured by image J and there was a significant difference between the PBS control group and the 0.5 mg/kg and 1 mg/kg melittin-administered groups (FIGS. 7C and 7D). This suggests that a decrease in population of tissue-resident M2-type tumor-associated macrophages suppresses angiogenesis. Therefore, it was confirmed that the melittin controls the tumor microenvironment to reduce the number of M2-type tumor-associated macrophages to exhibit an anti-cancer effect by suppressing angiogenesis around the tumor cells.

Comparative Example 1. Effects of M2-Type Tumor-Associated Macrophage by PLA2 Among Ingredients of Bee Venom 1-1. Preparation of Cell and Analysis of mRNA Expression Level 1-1-1. Preparation of Cell A murine BV-2 microglial cell line was maintained in an RPMI 1640 medium (Welgene, Gyeongsan, Korea) Technologies, Rockville, Md., USA) added with 10% fetal bovine serum (Welgene, Gyeongsan, Korea), 100 U ml$^{-1}$ penicillin, and 100 µgml$^{-1}$ streptomycin (Invitrogen Life, Invitrogen Life). The cells were cultured every 2 to 3 days until 80% confluent. In all experiments, the cells were cultured at 37° C. with 95% humidity and 5% $CO_2$. For differentiation, the cells were seeded in a 6-well plate at a density of 5×10$^5$ cells/ml and treated the next day. Immediately before treatment, the cells were washed twice with a serum-free RPMI medium and supplemented with 2 ml of a warm serum-free RPMI medium containing the experimental treatment. The cells were pretreated with 0.1, 1 or 10 pgml$^{-1}$ bvPLA2 for 30 minutes and then 1 µpgml$^{-1}$ lipopolysaccharide (LPS) (Sigma-Aldrich, St Louis, Mo., USA) or 20 ngml$^{-1}$ murine recombinant interleukin-4 (R & D Systems, Minneapolis, Minn., USA) was added to each well. After 24 hours of treatment, the cells were rinsed twice with PBS and collected for RNA extraction.

1-1-2. RNA Extraction and Quantitative Real-Time PCR Method

Total RNA was extracted from BV-2 cells using an Easy-BLUE RNA extraction kit (iNtRON Biotechnology, Inc., Seongnam, Korea). RNA quality and concentration were determined using a NanoDrop spectrophotometer (NanoDrop Technologies, Inc., ND-1000, Wilmington, Del., USA) and normalized to the lowest concentration with RNase-free water. RNA was reverse-transcribed into cDNA using CycleScript reverse transcriptase and random oligonucleotide primers (Bioneer, Daej eon, Korea) according to the manufacturer's instructions. Quantitative real-time PCR was performed using a SensiFAST SYBR No-ROX kit (Bioline, Taunton, Mass., USA) and analyzed with a Light-Cycler 480 system (Roche Ltd, Basel, Switzerland). The PCR reaction was repeated at 55 cycles of denaturation at 95° C. for 10 seconds, annealing at 72° C. for 10 seconds, and denaturation at 60° C. for 10 seconds and fluorescence was measured at the end of each cycle. Data were expressed in 2-ΔΔCT for experimental genes normalized to GAPDH and expressed in fold change compared with a saline-treated control group. The following primers were used: TNF-α for: 5'-TTCTGTCTACTGAACTTCGGGGTGATCGGTCC-3' (SEQ ID NO: 3); TNF-α rev: 5'-GTATGAGATAGCAAATCGGCTGACGGTGTGGG-3' (SEQ ID NO: 4); iNOS for: 5'-GGCAGCCTGTGAGACCTTTG-3' (SEQ ID NO: 15); iNOS rev: 5'-CATTGGAAGTGAAGCGTTTCG-3' (SEQ ID NO: 16); Arg1 for: 5'-AGACAGCAGAGGAGGTG AAGAG-3' (SEQ ID NO: 17); Arg1 rev: 5'-CGAAGCAAGCCAAGGTTAAAGC-3' (SEQ ID NO: 18); MMR for: 5'-AGTGGCAGGTGGCTTATG-3' (SEQ ID NO: 19); MMR rev: 5'-GGT TCAGGAGTTGTTGTG-3' (SEQ ID NO: 20); GAPDH for: 5'-ACCCAGAAGACTGT GGATGG-3' (SEQ ID NO: 1); GAPDH rev: 5'-CACATTGGGGGTAGGAACAC-3' (SEQ ID NO: 2)

1-2. Experimental Results

Figure 8:
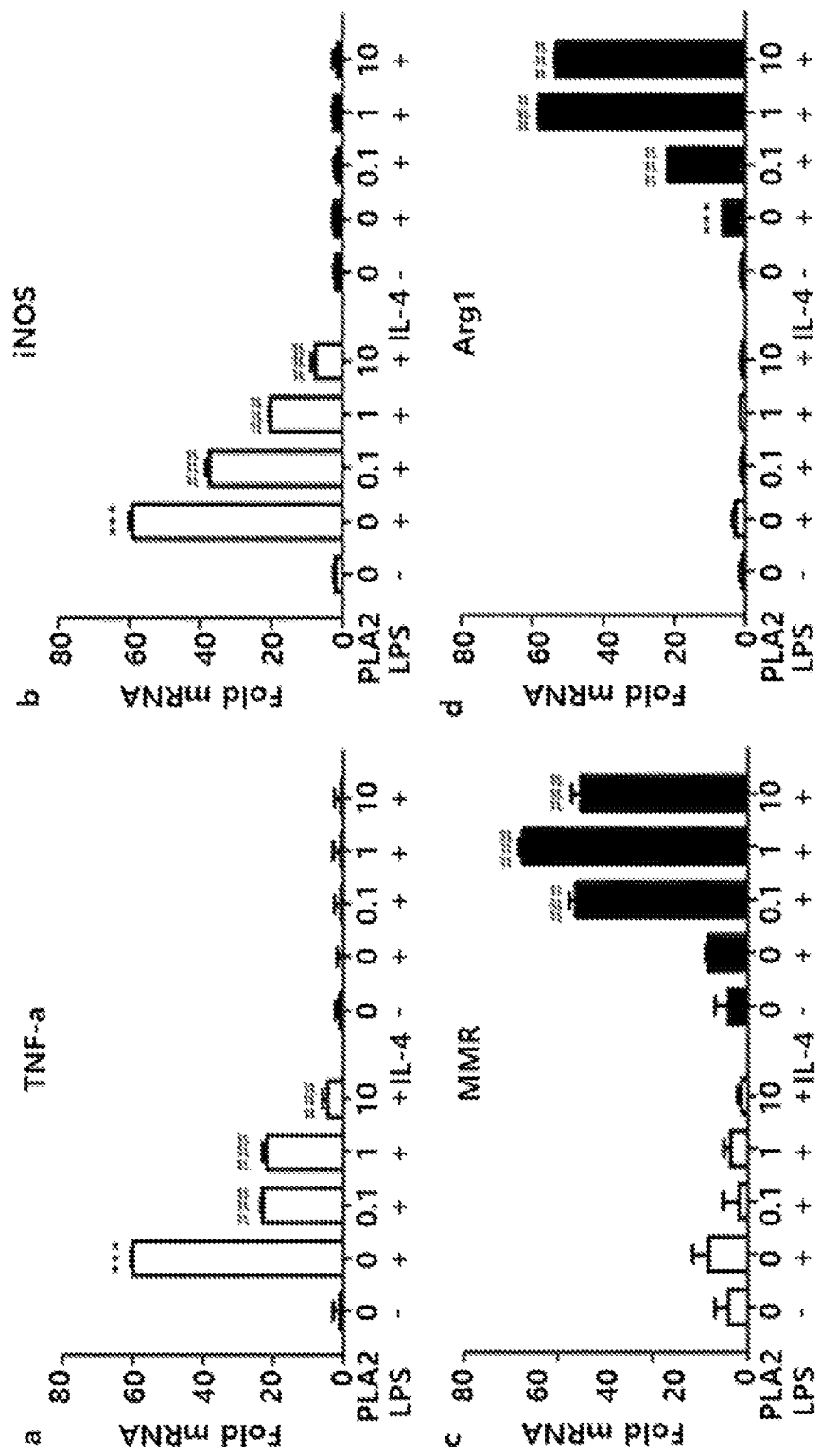
FIG. 8 illustrates an effect of inducing differentiation of M2 type macrophages by PLA2, another ingredient of bee venom.

We tested an effect of bvPLA2 on M1/M2 polarization of cerebellar cells by quantifying gene expression upon exposure to M1 induction conditions (LPS) or M2 induction conditions (IL-4). A tumor necrosis factor α (TNF-α) and inducible nitric oxide synthase (iNOS) act as an M1 phenotypic marker, while a macrophage mannose receptor (MMR, CD206) and arginase-1 (Arg1) act as an M2 marker. Messenger RNA (mRNA) of TNF-α and iNOS was significantly increased compared to a vehicle control group when the cells were exposed to LPS (FIG. 8). BvPLA2 effectively blocked the differentiation of BV-2 cells to the M1 phenotype in a dose dependent manner during LPS exposure. No change in M1 marker was observed during IL-4 exposure. MMR was slightly increased and Arg1 was significantly increased by IL-4 compared to a vehicle control group. When the cells were exposed to IL-4, both mRNA levels were significantly increased in bvPLA2 treatment. There was no significant difference in the M2 marker during LPS exposure. As a whole, these results show that bvPLA2 promotes the differentiation of M2 microglia. Therefore, PLA2, another major ingredient, rather promotes the differentiation into M2-type tumor-associated macrophages, and only melittin selectively suppresses the M2-type tumor-associated macrophages to control the tumor microenvironment, and as a result, it was confirmed that PLA2 may exhibit an anti-cancer effect by suppressing the growth and metastasis of the tumor.

It will be appreciated by those skilled in the art that the present invention as described above may be implemented into other specific forms without departing from the technical spirit thereof or essential characteristics. Thus, it is to be appreciated that embodiments described above are intended to be illustrative in every sense, and not restrictive. The scope of the present invention is represented by the claims to be described below rather than the detailed description, and it is to be interpreted that the meaning and scope of the claims and all the changes or modified forms derived from the equivalents thereof come within the scope of the present invention.

The invention claimed is:

1. A method for removing tumor-associated macrophage, or treating a tumor-associated macrophage-mediated disease, comprising administering a composition comprising melittin as an active ingredient to a subject in need thereof, wherein the subject requires treatment of suppressing the M2-type tumor-associated macrophage without affecting the M1-type tumor-associated macrophage, wherein the composition increases a ratio (M1/M2) of a M1-type tumor-associated macrophage to a M2-type tumor-associated macrophage as compared to a comparative case where the composition is not administered, wherein the composition suppresses expression of a gene and protein of CD31, and wherein the subject requires a treatment of suppressing a tumor growth without affecting a cell cycle of tumor cells.

2. The method according to claim 1, wherein a concentration of the melittin administered is 0.1 μg/ml to 2 μg/ml.

3. The method according to claim 1, wherein the tumor-associated macrophage is the M2-type tumor-associated macrophage.

4. The method according to claim 1, wherein the tumor-associated macrophage-mediated disease is Lewis lung cancer.

* * * * *

SEQUENCE LISTING

<160> NUMBER OF SEQ ID NOS: 20

<210> SEQ ID NO 1
<211> LENGTH: 20
<212> TYPE: DNA
<213> ORGANISM: Artificial Sequence
<220> FEATURE:
<223> OTHER INFORMATION: Gapdh forward

```
<400> SEQUENCE: 1
acccagaaga ctgtggatgg                                              20

<210> SEQ ID NO 2
<211> LENGTH: 20
<212> TYPE: DNA
<213> ORGANISM: Artificial Sequence
<220> FEATURE:
<223> OTHER INFORMATION: Gapdh reverse

<400> SEQUENCE: 2
cacattgggg gtaggaacac                                              20

<210> SEQ ID NO 3
<211> LENGTH: 32
<212> TYPE: DNA
<213> ORGANISM: Artificial Sequence
<220> FEATURE:
<223> OTHER INFORMATION: Tnf-a forward

<400> SEQUENCE: 3
ttctgtctac tgaacttcgg ggtgatcggt cc                                32

<210> SEQ ID NO 4
<211> LENGTH: 32
<212> TYPE: DNA
<213> ORGANISM: Artificial Sequence
<220> FEATURE:
<223> OTHER INFORMATION: Tnf-a reverse

<400> SEQUENCE: 4
gtatgagata gcaaatcggc tgacggtgtg gg                                32

<210> SEQ ID NO 5
<211> LENGTH: 18
<212> TYPE: DNA
<213> ORGANISM: Artificial Sequence
<220> FEATURE:
<223> OTHER INFORMATION: Mrc1/CD206 forward

<400> SEQUENCE: 5
agtggcaggt ggcttatg                                                18

<210> SEQ ID NO 6
<211> LENGTH: 18
<212> TYPE: DNA
<213> ORGANISM: Artificial Sequence
<220> FEATURE:
<223> OTHER INFORMATION: Mrc1/CD206 reverse

<400> SEQUENCE: 6
ggttcaggag ttgttgtg                                                18

<210> SEQ ID NO 7
<211> LENGTH: 20
<212> TYPE: DNA
<213> ORGANISM: Artificial Sequence
<220> FEATURE:
<223> OTHER INFORMATION: Il-10 forward

<400> SEQUENCE: 7
ataactgcac ccacttccca                                              20

<210> SEQ ID NO 8
<211> LENGTH: 20
```

```
<212> TYPE: DNA
<213> ORGANISM: Artificial Sequence
<220> FEATURE:
<223> OTHER INFORMATION: Il-10 reverse

<400> SEQUENCE: 8
tcatttccga taaggcttgg                                          20

<210> SEQ ID NO 9
<211> LENGTH: 21
<212> TYPE: DNA
<213> ORGANISM: Artificial Sequence
<220> FEATURE:
<223> OTHER INFORMATION: Tgf-B forward

<400> SEQUENCE: 9
gaaggcagag ttcagggtct t                                        21

<210> SEQ ID NO 10
<211> LENGTH: 21
<212> TYPE: DNA
<213> ORGANISM: Artificial Sequence
<220> FEATURE:
<223> OTHER INFORMATION: Tgf-B reverse

<400> SEQUENCE: 10
ggttcctgtc tttgtggtga a                                        21

<210> SEQ ID NO 11
<211> LENGTH: 22
<212> TYPE: DNA
<213> ORGANISM: Artificial Sequence
<220> FEATURE:
<223> OTHER INFORMATION: Flt1/VEGFR1 reverse

<400> SEQUENCE: 11
ggagatcctt cgaggagcac tt                                       22

<210> SEQ ID NO 12
<211> LENGTH: 25
<212> TYPE: DNA
<213> ORGANISM: Artificial Sequence
<220> FEATURE:
<223> OTHER INFORMATION: Vegf reverse

<400> SEQUENCE: 12
ggcgatttag cagcagatat aagaa                                    25

<210> SEQ ID NO 13
<211> LENGTH: 22
<212> TYPE: DNA
<213> ORGANISM: Artificial Sequence
<220> FEATURE:
<223> OTHER INFORMATION: Flt1/VEGFR1 forward

<400> SEQUENCE: 13
acattggtgg tggctgactc tc                                       22

<210> SEQ ID NO 14
<211> LENGTH: 20
<212> TYPE: DNA
<213> ORGANISM: Artificial Sequence
<220> FEATURE:
<223> OTHER INFORMATION: Flt1/VEGFR1 reverse

<400> SEQUENCE: 14
```

```
cctctccttc ggctggcatc                                              20

<210> SEQ ID NO 15
<211> LENGTH: 20
<212> TYPE: DNA
<213> ORGANISM: Artificial Sequence
<220> FEATURE:
<223> OTHER INFORMATION: iNOS forward

<400> SEQUENCE: 15
ggcagcctgt gagacctttg                                              20

<210> SEQ ID NO 16
<211> LENGTH: 21
<212> TYPE: DNA
<213> ORGANISM: Artificial Sequence
<220> FEATURE:
<223> OTHER INFORMATION: iNOS reverse

<400> SEQUENCE: 16
cattggaagt gaagcgtttc g                                            21

<210> SEQ ID NO 17
<211> LENGTH: 22
<212> TYPE: DNA
<213> ORGANISM: Artificial Sequence
<220> FEATURE:
<223> OTHER INFORMATION: Arg1 forward

<400> SEQUENCE: 17
agacagcaga ggaggtgaag ag                                           22

<210> SEQ ID NO 18
<211> LENGTH: 22
<212> TYPE: DNA
<213> ORGANISM: Artificial Sequence
<220> FEATURE:
<223> OTHER INFORMATION: Arg1 reverse

<400> SEQUENCE: 18
cgaagcaagc caaggttaaa gc                                           22

<210> SEQ ID NO 19
<211> LENGTH: 18
<212> TYPE: DNA
<213> ORGANISM: Artificial Sequence
<220> FEATURE:
<223> OTHER INFORMATION: MMR forward

<400> SEQUENCE: 19
agtggcaggt ggcttatg                                                18

<210> SEQ ID NO 20
<211> LENGTH: 18
<212> TYPE: DNA
<213> ORGANISM: Artificial Sequence
<220> FEATURE:
<223> OTHER INFORMATION: MMR reverse

<400> SEQUENCE: 20
ggttcaggag ttgttgtg                                                18
```